(12) United States Patent
Heinz et al.

(10) Patent No.: US 9,918,806 B2
(45) Date of Patent: Mar. 20, 2018

(54) MACHINING OF CERAMIC MATERIALS

(71) Applicant: Ivoclar Vivadent AG, Schaan (LI)

(72) Inventors: Markus Heinz, Naturns (IT); Klaus Rinner, Naturns (IT); Georg Gorfer, Naturns (IT); Marius Aster, Naturns (IT); Marcel Schweiger, Chur (CH); Dmitri Brodkin, Livingston, NJ (US)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/826,639

(22) Filed: Aug. 14, 2015

(65) Prior Publication Data

US 2015/0351880 A1 Dec. 10, 2015

Related U.S. Application Data

(60) Continuation of application No. 13/467,260, filed on May 9, 2012, now Pat. No. 9,220,576, which is a
(Continued)

(30) Foreign Application Priority Data

Aug. 7, 2003 (DE) .................................. 103 36 913

(51) Int. Cl.
| | |
|---|---|
| B24B 49/00 | (2012.01) |
| A61C 3/02 | (2006.01) |
| A61C 13/08 | (2006.01) |
| A61C 8/00 | (2006.01) |
| A61C 13/00 | (2006.01) |
| A61C 5/70 | (2017.01) |
| A61C 5/77 | (2017.01) |
| A61C 13/083 | (2006.01) |

(52) U.S. Cl.
CPC .................. *A61C 3/02* (2013.01); *A61C 5/70* (2017.02); *A61C 5/77* (2017.02); *A61C 8/005* (2013.01); *A61C 13/0003* (2013.01); *A61C 13/0004* (2013.01); *A61C 13/0022* (2013.01); *A61C 13/082* (2013.01); *A61C 13/083* (2013.01); *Y10T 29/49567* (2015.01); *Y10T 428/24479* (2015.01)

(58) Field of Classification Search
USPC ................ 451/5, 11, 12; 433/72, 74, 75, 76; 428/542.8
See application file for complete search history.

(56) References Cited

U.S. PATENT DOCUMENTS

| | | | |
|---|---|---|---|
| 2,684,911 | A | 7/1954 | Stookey |
| 3,006,775 | A | 10/1961 | Chen |

(Continued)

FOREIGN PATENT DOCUMENTS

| | | | |
|---|---|---|---|
| CA | 2213390 | A1 | 3/1998 |
| CA | 2252660 | A1 | 5/1999 |

(Continued)

OTHER PUBLICATIONS

Durschang, Dr. Bernhard, "Report of Results", Fraunhofer Institute for Silicate Research ISC Glass and Mineral Materials, 2015.
(Continued)

*Primary Examiner* — Joseph J Hail
*Assistant Examiner* — Shantese McDonald
(74) *Attorney, Agent, or Firm* — Ann M. Knab; Thad McMurray

(57) ABSTRACT

Milling strategies for machining dental ceramic materials are provided that reduce milling time while maintaining strength, accuracy and marginal integrity.

5 Claims, 15 Drawing Sheets

Related U.S. Application Data continuation-in-part of application No. 13/096,367, filed on Apr. 28, 2011, now Pat. No. 8,197,299, which is a continuation of application No. 12/562,348, filed on Sep. 18, 2009, now Pat. No. 7,955,159, which is a continuation-in-part of application No. 11/935,203, filed on Nov. 5, 2007, now Pat. No. 8,047,021, which is a division of application No. 10/913,095, filed on Aug. 6, 2004, now Pat. No. 7,316,740.

(56) References Cited

U.S. PATENT DOCUMENTS

| | | | |
|---|---|---|---|
| 3,022,180 | A | 2/1962 | Morrissey |
| 3,161,528 | A | 12/1964 | Eppler |
| 3,252,778 | A | 5/1966 | Goodman et al. |
| 3,804,608 | A | 4/1974 | Gaskell et al. |
| 3,816,704 | A | 6/1974 | Borom et al. |
| 3,977,857 | A | 8/1976 | Mattox |
| 4,155,888 | A | 5/1979 | Mooth |
| 4,189,325 | A | 2/1980 | Barrett et al. |
| 4,414,282 | A | 11/1983 | McCollister et al. |
| 4,473,653 | A | 9/1984 | Rudoi |
| 4,480,044 | A | 10/1984 | McAlinn |
| 4,515,634 | A | 5/1985 | Wu et al. |
| 4,671,770 | A | 6/1987 | Bell et al. |
| 4,963,707 | A | 10/1990 | Zyokou et al. |
| 4,977,114 | A | 12/1990 | Horinouchi et al. |
| 5,176,961 | A | 1/1993 | Crooker et al. |
| 5,219,799 | A | 6/1993 | Beall et al. |
| 5,306,278 | A * | 4/1994 | Dahl ............ A61B 17/17 408/241 G |
| 5,507,981 | A | 4/1996 | Petticrew |
| 5,628,564 | A | 5/1997 | Nenyei et al. |
| 5,691,256 | A | 11/1997 | Taguchi et al. |
| 5,698,482 | A | 12/1997 | Frank et al. |
| 5,702,514 | A | 12/1997 | Petticrew |
| 5,707,777 | A | 1/1998 | Aoai et al. |
| 5,872,069 | A | 2/1999 | Abe |
| 5,874,376 | A | 2/1999 | Taguchi et al. |
| 5,938,959 | A | 8/1999 | Wang |
| 5,968,856 | A | 10/1999 | Schweiger et al. |
| 6,066,584 | A | 5/2000 | Krell et al. |
| 6,095,682 | A | 8/2000 | Hollander et al. |
| 6,106,747 | A | 8/2000 | Wohlwend |
| 6,121,175 | A | 9/2000 | Drescher et al. |
| 6,048,589 | A | 11/2000 | Suzuki |
| 6,157,004 | A | 12/2000 | Bizzio |
| 6,163,020 | A | 12/2000 | Bartusch et al. |
| 6,174,827 | B1 | 1/2001 | Goto et al. |
| 6,252,202 | B1 | 6/2001 | Zychek |
| 6,267,595 | B1 | 7/2001 | Gratz |
| 6,270,876 | B1 | 8/2001 | Abe et al. |
| 6,287,121 | B1 | 9/2001 | Guiot et al. |
| 6,342,458 | B1 | 1/2002 | Schweiger et al. |
| 6,376,397 | B1 | 4/2002 | Petticrew |
| 6,420,288 | B2 | 7/2002 | Schweiger et al. |
| 6,441,346 | B1 | 8/2002 | Zychek |
| 6,455,451 | B1 | 9/2002 | Brodkin et al. |
| 6,485,849 | B2 | 11/2002 | Petticrew |
| 6,514,893 | B1 | 2/2003 | Schweiger et al. |
| 6,517,623 | B1 | 2/2003 | Brodkin et al. |
| 6,593,257 | B1 | 7/2003 | Nagata et al. |
| 6,802,894 | B2 | 10/2004 | Brodkin et al. |
| 6,818,573 | B2 | 11/2004 | Petticrew |
| 6,913,463 | B2 * | 7/2005 | Blacklock ............ A61B 17/176 408/115 R |
| 7,162,321 | B2 | 1/2007 | Luthardt et al. |
| 7,316,740 | B2 | 1/2008 | Rheinberger et al. |
| 7,452,836 | B2 | 11/2008 | Apel et al. |
| 7,655,586 | B1 | 2/2010 | Brodkin et al. |
| 7,806,694 | B2 | 10/2010 | Brodkin et al. |
| 7,816,291 | B2 | 10/2010 | Schweiger et al. |
| 7,867,930 | B2 | 1/2011 | Apel et al. |
| 7,867,933 | B2 | 1/2011 | Apel et al. |
| 7,871,948 | B2 | 1/2011 | Apel et al. |
| 7,892,995 | B2 | 2/2011 | Castillo |
| 7,993,137 | B2 | 8/2011 | Apel et al. |
| 8,042,358 | B2 | 10/2011 | Schweiger et al. |
| 8,047,021 | B2 | 11/2011 | Schweiger et al. |
| 8,241,297 | B2 * | 8/2012 | Ashman ............ A61B 17/1796 206/206 |
| 8,444,756 | B2 | 5/2013 | Schweiger et al. |
| 2001/0006174 | A1 | 7/2001 | Brennan |
| 2001/0031446 | A1 | 10/2001 | Petticrew |
| 2002/0010063 | A1 | 1/2002 | Schweiger et al. |
| 2002/0022563 | A1 | 2/2002 | Schweiger et al. |
| 2002/0031670 | A1 | 3/2002 | Goto et al. |
| 2002/0035025 | A1 | 3/2002 | Schweiger et al. |
| 2002/0160694 | A1 | 10/2002 | Wood et al. |
| 2003/0073563 | A1 | 4/2003 | Brodkin et al. |
| 2004/0182538 | A1 | 9/2004 | Labrecht |
| 2005/0098064 | A1 | 5/2005 | Schweiger et al. |
| 2005/0127544 | A1 | 6/2005 | Brodkin et al. |
| 2006/0082033 | A1 | 4/2006 | Hauptmann et al. |
| 2006/0139091 | A1 | 6/2006 | Fratti |
| 2006/0257823 | A1 | 11/2006 | Pfeiffer et al. |
| 2006/0257824 | A1 | 11/2006 | Pfeiffer et al. |
| 2007/0023971 | A1 | 2/2007 | Saha et al. |
| 2008/0120994 | A1 | 5/2008 | Schweiger |
| 2008/0199823 | A1 | 8/2008 | Miller |
| 2009/0023574 | A1 | 1/2009 | Holand et al. |
| 2009/0038344 | A1 | 2/2009 | Apel et al. |
| 2009/0038508 | A1 | 2/2009 | Apel et al. |
| 2009/0042166 | A1 | 2/2009 | Craig et al. |
| 2009/0256274 | A1 | 10/2009 | Castillo |
| 2009/0258778 | A1 | 10/2009 | Castillo |
| 2010/0083706 | A1 | 4/2010 | Castillo |
| 2011/0256409 | A1 | 10/2011 | Ritzberger et al. |
| 2012/0094822 | A1 | 4/2012 | Castillo et al. |
| 2012/0148988 | A1 | 6/2012 | Castillo et al. |
| 2012/0248642 | A1 | 10/2012 | Ritzberger et al. |
| 2012/0309607 | A1 | 12/2012 | Durschang |
| 2013/0161915 | A1 * | 6/2013 | Johnson ............ B23Q 13/00 279/142 |
| 2014/0141960 | A1 | 5/2014 | Borczuch-Laczka et al. |

FOREIGN PATENT DOCUMENTS

| | | |
|---|---|---|
| DE | 1696473 B1 | 8/1970 |
| DE | 2451121 | 1/1974 |
| DE | 2949619 A1 | 11/1980 |
| DE | 4303458 C1 | 1/1994 |
| DE | 19750794 A1 | 6/1999 |
| DE | 202009018951 U1 | 9/2014 |
| DE | 202009018953 U1 | 9/2014 |
| EP | 0536479 A1 | 4/1993 |
| EP | 0536572 A1 | 4/1993 |
| EP | 0827941 A1 | 3/1998 |
| EP | 0817597 B1 | 9/1999 |
| EP | 1127564 A2 | 8/2001 |
| EP | 1152641 A2 | 11/2001 |
| EP | 0774933 | 12/2001 |
| EP | 1505041 A1 | 2/2005 |
| GB | 752243 A | 7/1956 |
| GB | 2284655 A | 6/1995 |
| JP | 32-5080 | 7/1932 |
| JP | H10323354 A | 12/1998 |
| JP | 11-74418 A | 3/1999 |
| JP | 2005-062832 A | 3/2005 |
| JP | 5094017 B2 | 12/2012 |
| WO | 9532678 A2 | 12/1995 |
| WO | 0228802 A2 | 4/2002 |
| WO | 2006042046 A2 | 4/2006 |
| WO | 2007028787 A1 | 3/2007 |
| WO | 2012143137 A1 | 10/2012 |

OTHER PUBLICATIONS

McMillan, P.W., et al., "The Structure and Properties of a Lithium Zinc Silicate Glass-Ceramic," Journal of Material Science 1966, I. 269-279.

(56) References Cited

OTHER PUBLICATIONS

Deubener, J., et al., "Induction time analysis of nucleation and crystal grown in di- and metasilicate glasses," Journal of Non-Crystalline Solids 1993, 163, 1-12.
Holand, W. et al., "Glass-ceramic technology", American Chemical Society 2002, Westerville OH, USA.
Holand, W. et al., "Control of nucleation in glass ceramics", Phil. Trans. Soc. Lond. A 2003, 361, 575-589.
Holand, W. et al., "Principles and phenomena of bioengineering with glass-ceramics of dental restoration", Journal of the European Ceramics Society 2007, 27, 1571-1577.
Apel, E., et al., "Influence of Zr02 on the crystallization and properties of lithium disilicate glass-ceramics derived from multi-component system", Journal of European Ceramic Society, 2007, 27, 1571-1577.
Ivoclar Vivadent Inc., IPS e.max lithium disilicate, 627329, Rev. Feb. 2009.
Montedo et al., "Low Thermal Expansion Sintered LZSA Glass-Ceramics," American Ceramic Society Bulletin, vol. 87, No. 7, pp. 34-40.
Giassi, et al., "Injection Moulding of LiO2—ZrO2—SiO2—A12O3 (LZSA) Glass Ceramics," Glass Technol., 46(3), 277-280 (2005).
http://enwikipedia.org/wiki/Nucleation; Sep. 20, 2012.
Borom et al., "Strength and Microstructure in Lithium Disilicate Glass-Ceramics." J. Am. Ceram. Soc. 58 (9-10):1 385-391 (1975).
Stookey, S.D., "Chemical Machining of Photosensitive Glass," Ind. Eng. Chem. 45:115-118 (1993).
Von Clausbruch et al., "The effect of P2O5 on the Crystallization and Microstructure of Glass-Ceramics in the SiO2—3 Li2O—K2O—ZnO—P2O5 System," J. Non-Crystalline Solids 263&264: 388-394 (2000).
Von Clausbruch et al., Effect of ZnO on the Crystallization, Microstructure, and Properties of Glass-Ceramics in the 4 SiO2—Li2O—ZnO—K2O—P2O5 System, Glastech. Ber. Glass Sci. Technol. 74(8):223-229 (2001).
Oliveira et al., "Sintering and Crystallization of GlassPowder in Li2O—ZrO2—SiO2 System," J. Amer. Ceramic Soc. 81 5 (3): 777-780 (1998).
European Search Report for EP Application No. 10171839.3, dated Jan. 25, 2011.

\* cited by examiner

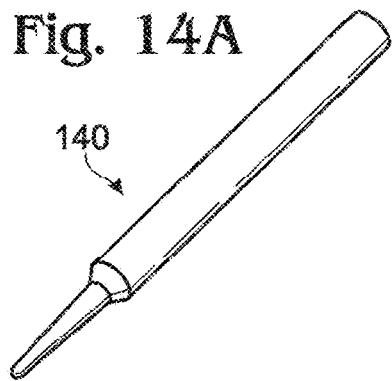
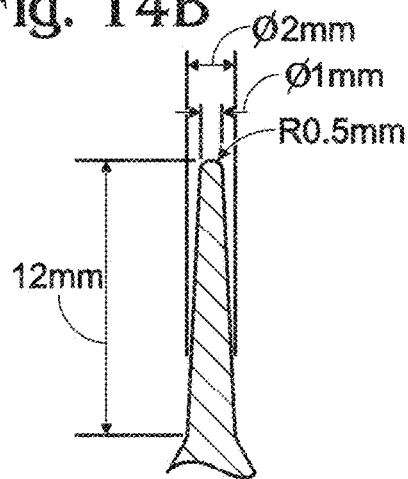
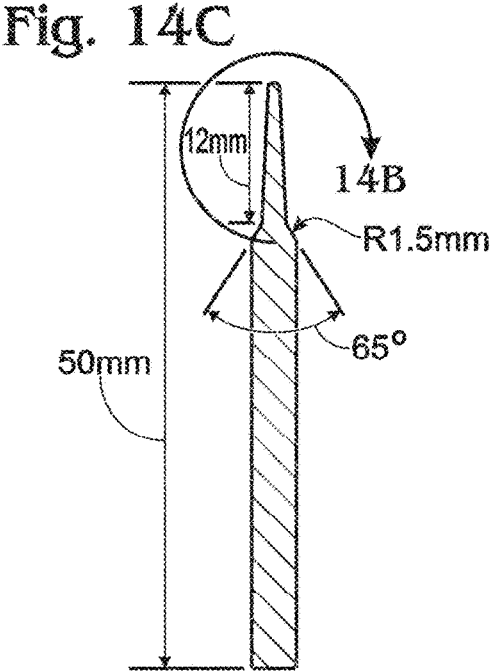
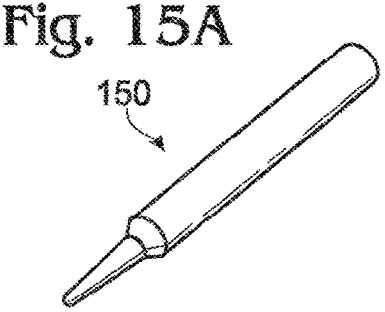
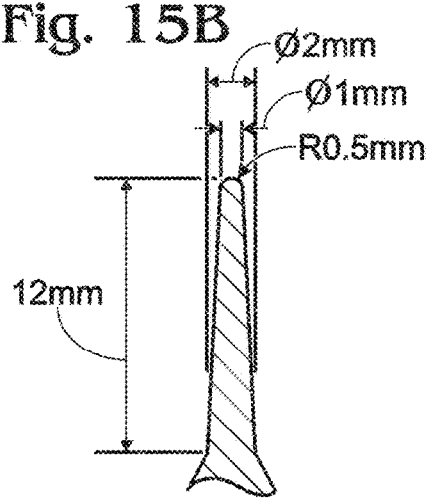

MACHINING OF CERAMIC MATERIALS

CROSS-REFERENCE TO RELATED APPLICATIONS

This application is a continuation application of U.S. patent application Ser. No. 13/467,260, filed May 9, 2012, which is a continuation-in-part of U.S. patent application Ser. No. 13/096,367, filed Apr. 28, 2011, which is a continuation of U.S. patent application Ser. No. 12/562,348, filed Sep. 18, 2009, now U.S. Pat. No. 7,955,159, which is a continuation in part of U.S. patent application Ser. No. 11/935,203, filed Nov. 5, 2007, now U.S. Pat. No. 8,042,358, which is of division of U.S. patent application Ser. No. 10/913,095, filed Aug. 6, 2004, now U.S. Pat. No. 7,316,740, which claims priority to German Patent Application Serial No. 103 36 913.9, filed Aug. 7, 2003, all of which are herein incorporated by reference in their entirety.

FIELD OF THE INVENTION

The invention relates to lithium silicate materials which can be easily shaped by machining and subsequently converted into shaped products with high strength.

BACKGROUND OF THE INVENTION

There is an increasing demand for materials which can be processed into dental restorative products, such as crowns, inlays and bridges, by means of computer controlled milling machines. Such CAD/CAM methods are very attractive as they allow to provide the patient quickly with the desired restoration. A so-called chair-side treatment is thus possible for the dentist.

However, materials suitable for processing via computer aided design/computer aided machining (CAD/CAM) methods have to meet a very specific profile of properties.

First of all, they need to have in the finally prepared restoration appealing optical properties, such as translucence and shade, which imitate the appearance of the natural teeth. They further need to show high strength and chemical durability so that they can take over the function of the natural tooth material and maintain these properties over a sufficient period of time while being permanently in contact with fluids in the oral cavity which can even be aggressive, such as acidic in nature.

Secondly and very importantly, it should be possible to machine them in an easy manner into the desired shape without undue wear of the tools and within short times. This property requires a relatively low strength of the material and is therefore in contrast to the desired properties mentioned above for the final restoration.

The difficulty of combining the properties of low strength in the stage of the material to be processed and a high strength of the final restoration is reflected by the known materials for a CAD/CAM processing which are in particular with respect to an easy machinability unsatisfactory.

DE-A-197 50 794 discloses lithium disilicate glass ceramics which are primarily intended to be shaped to the desired geometry by a hot-pressing process wherein the molten material is pressed in the viscous state. It is also possible for these materials to be shaped by computer aided milling processes. However, it has been shown that the machining of these materials results in a very high wear of the tools and very long processing times. These disadvantages are caused by the high strength and toughness primarily imparted to the materials by the lithium disilicate crystalline phase. Moreover, it has been shown that the machined restorations show only a poor edge strength. The term "edge strength" refers to the strength of parts of the restoration having only a small thickness in the range of few $\frac{1}{10}$ mm.

Further approaches of achieving easy machinability together with a high strength of the final restoration have also been made. EP-B-774 993 and EP-B-817 597 describe ceramic materials on the basis of $Al_2O_3$ or $ZrO_2$ which are machined in an unsintered state which is also referred to as "green state". Subsequently, the green bodys are sintered to increase the strength. However, these ceramic materials suffer from a drastical shrinkage of up to 50% by volume (or up to 30% as linear shrinkage) during the final sintering step. This leads to difficulties in preparing the restorations with exactly the dimensions as desired. The substantial shrinkage represents a particular problem if complicated restorations are manufactured, such as a multi-span bridge.

From S. D. Stookey: "Chemical Machining of Photosensitive Glass", *Ind. Eng. Chem.*, 45, 115-118 (1993) and S. D. Stookey: "Photosensitivity Opacifiable Glass" U.S. Pat. No. 2,684,911 (1954) it is also known that in lithium silicate glass ceramics a. metastable phase can be formed at first. For example in photosensitive glass ceramics (Fotoform®, FotoCeram®) Ag-particles are formed using UV-light. These Ag-particles serve as crystallization agent in a lithium metasilicate phase. The areas which were exposed to light are in a subsequent step washed out by diluted HF. This procedure is possible since the solubility of the lithium metasilicate phase in HF is much higher than the solubility of the parent glass. The glass portion remaining after said solubilizing process (Fotoform®) can be transferred into a lithium disilicate glass ceramic (FotoCeram®) by an additional heat treatment.

Also investigations of Borom, e.g. M.-P. Borom, A. M. Turkalo, R. H. Doremus: "Strength and Microstructure In Lithium Disilicate Glass-Ceramics", *J. Am. Ceream. Soc.*, 58, No. 9-10, 385-391 (1975) and M.-P. Borom, A. M. Turkalo, R. H. Doremus: "Verfahren zum Herstellen von Glaskeramiken" DE-A-24 51 121 (1974), show that a lithium disilicate glass ceramic can in the first instance crystallize in varying amounts as metastable lithium metasilicate phase. However, there also exist compositions which crystallize in the form of the disilicate phase from the beginning and the metasilicate phase is not present at all. A systematic investigation of this effect has not become known. From the investigations of Borom it is also known that the glass ceramic which contains lithium metasilicate as the main phase has a reduced strength compared to the one of a glass ceramic which only contains a lithium disilicate phase.

Thus, the prior art materials show a couple of shortcomings. It is, therefore, an object of the present invention to eliminate these disadvantages and in particular to provide a material which, above all, can be easily shaped by computer-aided milling and trimming processes and can subsequently be converted into high-strength dental products which also display a high chemical durability and excellent optical properties and exhibit a drastically reduced shrinkage during said final conversion.

SUMMARY OF THE INVENTION

This object is achieved by the lithium silicate glass ceramic material of the present invention.

The invention also relates to a lithium disilicate material, dental articles comprising lithium disilicate, processes for manufacturing of lithium silicate ingots and blanks convertible to lithium disilicate and their uses for fabrication of dental restorations utilizing heat (hot) pressing and CAD/CAM, a lithium silicate glass and uses thereof, and methods for manufacturing lithium silicate dental articles and dental restorations.

In particular this invention is related to methods of mass-production of dental restorations using lithium silicate blanks and at least 4-axis or greater CNC machines. More specifically this invention is related to milling strategies especially useful for machining lithium silicate blanks using 5-axis or greater CNC machines equipped with robotic and automated loading features.

Additional aspects of the embodiments of the invention are directed to a method of reducing the time for machining a dental ceramic blank, wherein the fracture toughness ($K_{Ic}$) and the flexural strength ($\sigma_f$) of the dental ceramic material are known, comprising calculating an estimate of the maximal surface critical flaw size and an estimate of the maximal volume critical flaw size of the dental ceramic using the following formula:

$$c = (K_{Ic}/\sigma_f)^2$$

wherein: c is the maximal surface critical flaw size; and 2c is the maximal volume critical flaw size.

Further aspects of the method include implementing a machining strategy using a series of diamond tools, wherein the diamond tools comprise embedded diamonds; wherein the machining strategy comprises rough, intermediate and fine machining steps; wherein each step comprises a tool path and machining parameters; wherein the tool path and machining parameters are carried out by at least one of the series of diamond tools; wherein the grain size of the embedded diamonds is larger than approximately the estimated maximal size of the surface critical flaw and smaller than approximately the estimated maximal size of the volume critical flaw.

According to a further embodiment of the present invention, a machining strategy for machining a dental ceramic blank into a dental article is provided, wherein the fracture toughness ($K_{Ic}$) and the flexural strength ($\sigma_f$) of the dental ceramic material are known, comprising calculating an estimate of the maximal surface critical flaw size and an estimate of the maximal volume critical flaw size of the dental ceramic using the following formula:

$$c = (K_{Ic}/\sigma_f)^2$$

wherein: c is the maximal surface critical flaw size and 2c is the maximal volume critical flaw size.

Further aspects of the method include determining the number of machining steps needed to mill the dental ceramic blank into the dental article by comparing the corresponding CAD file to the chosen blank geometry and material properties, defining milling parameters and computing the tool path for each machining step. Tool paths and machining parameters for all the machining steps required to mill a dental article are stored as a file called hereinafter CAM file. CAM file comprises specific commands and GO codes for a given CNC machine to execute all the required machining steps and associated tool paths to mill a dental article. In one of the preferred embodiments this is done by the process of mapping the shape to be milled (i.e. CAD file) onto a selected blank to establish the volume to be removed, which is then separated into regions requiring different accuracy and surface roughness. The regions are allocated to one or more of a rough machining, intermediate machining and fine machining step. The specific tool path is then calculated for each of the allocated machining steps and converted as a series of commands (GO codes) for CNC control unit (controller). Each machining step comprises tool path, machining parameters and tool selection and is implemented using at least one of a series of diamond tools for each machining step, wherein the diamond tools comprise embedded diamonds; wherein the grain size of the embedded diamonds is larger than approximately the estimated maximal value of the surface critical flaw size and smaller than approximately the estimated maximal value of the volume critical flaw size. Machining parameters comprise CNC machine (milling unit of a CAD/CAM system) settings critical for its operation and tool path computations such as RPM (revolutions per minute), feed rate (mm/min), tool geometry or length and diameter (mm), diamond tool grain size or grit (microns), depth of cut or lateral lining (microns), feed per revolution (microns). Depth of cut is normally set to be lower than the grain size of the embedded diamonds. The following principals are unique and critical for the milling strategy of the present invention: depths of cut are selected for fine machining to be less than the estimated maximal surface critical flaw size while depth of cut for rough machining is roughly equal or slightly larger than the estimated maximal surface critical flaw size. Feed rate per revolution is nearly always (except for special "Prep_fini" fine finishing steps to finesse the margin of the restoration) smaller than the depth of cut to minimize contact stresses on the tool, which include, work piece interface, shear (pull-out) stresses on embedded diamonds and tool wear. The aforementioned milling strategy, principals and approaches implemented as software instructions for selecting and computing optimal machining parameters and tool paths specific for each given material is hereinafter called template, for example lithium silicate template or leucite glass-ceramic template.

Milling with diamond tools (grinding) is quite different from milling with fluted tools (cutting). Diamond tools either comprise a coating with embedded diamonds or a matrix with embedded diamonds dispersed through the whole thickness of a tool. In both cases, embedded diamonds are characterized by a grain size distribution, range of grain sizes, grit size, and/or average grain size. Very often embedded diamonds are referred to as diamond grit. During machining, high contact stresses are generated on the interface between a work-piece and a tool. With all things being equal, it is beneficial to minimize the level of those stresses while maximizing material removal rate. The local stress condition on the milled surface in immediate contact with the diamond tool is very complex and is characterized by a stress tensor with all nine components changing in time. When a chip of material is cleaved away by the advancing diamond, the strain energy is released and when the next diamond hits the milled surface the stress begins building up again. It should be noted that many of these stress tensor components are parasitic and do not contribute to the effective machining process by cleaving off chips of material, but rather to tool wear by diamond pull-out. The volume of material to be removed is provided by subtracting the net shape of the dental article to be milled from the blank shape and separating it into regions requiring different material removal rates, accuracy and surface roughness. The regions are allocated to one or more of a rough, intermediate and fine machining step along with a specific tool path, which is calculated for each of the allocated machining steps. The purpose of the rough machining step is to approximate to the near net shape in the minimum amount of time (accuracy and surface roughness are not important). Intermediate machining is utilized to get closer to the net shape and is sufficient where surface roughness and accuracy are not so important (e.g., such as with the internal lateral surfaces of the coping or crown, which will be ultimately sealed by cement or adhesive). Fine machining is required for high accuracy and for a fine surface finish, such as at the margin of the restoration underside, which will carry most of the global loading. It was found that there is a synergy between simultaneous 5-axis milling and the use of conical diamond tools having round tips, allowing an optimal "angle of attack" to avoid introduction of dangerous, strength limiting flaws and allow more aggressive grinding. As a result, feed rates and material removal rates are maximized without noticeable compromise in strength. The rough, intermediate and fine machining steps are further dependent on the difference in volume of the dental ceramic blank and the machined net shape of the dental article and further dependent on the final roughness and accuracy of the machined net shape.

In further aspects, the dental article may comprise an inside surface, an outside surface and a preparation line and the machining steps may include one or more of the following: drilling an inside surface of the ceramic blank, milling an inside surface of the ceramic blank, milling the preparation line inside the ceramic blank, milling the preparation line outside the ceramic blank, drilling the outside surface of the ceramic blank, and milling the outside surface of the ceramic blank. Machining may include drilling, milling, cutting, grinding or a combination thereof.

In other aspects, the tools used herein may have diameters that range from approximately 0.5 mm to approximately 3.0 mm. The grain size of the diamonds embedded in the tools may range from approximately 60 microns to approximately 150 microns, or from about 90 to about 130 microns.

In additional aspects, the machining parameters may include tool specifications, revolutions per minute, linear speeds, feed rate (mm/min), feed per rotation (microns), depth of cut (microns) and material removal rate. Possible ranges for revolutions per minute (RPM) are from 30,000 to 100,000 revolutions per minute and preferably from 30,000 to 60,000 revolutions per minute. Possible ranges of the feed rate include approximately 500 mm/min to approximately 5000 mm/min. The depth of cut may range from approximately 10 microns to approximately 150 microns, preferably from about 10 microns to about 130 microns. It is preferable that the depth of cut is smaller than the grain size of the embedded diamonds and that the feed per rotation is smaller than the depth of cut. It is further preferable that the depth of cut is smaller than the estimated maximal value of the surface critical flaw size for fine machining and larger than the estimated maximal value of the surface critical flaw size for rough machining. The series of tools may include conical diamond tools having round tips and coated with diamond grains having different sizes. The conical form gives the grinding device much more rigidity against vibrations. The machining strategy in combination with the series of diamond tools reduce machining time while maintaining strength, accuracy and marginal integrity. For certain types of machinable ceramic materials carbide tools may also be used.

In further aspects, the machining process includes the use of computer files, wherein a first computer file comprises the specifications of the dental article to be machined and wherein the machining tool path is determined from the specifications in the first computer file. The dental ceramic blank comprises a geometry and material properties and the specifications of the first computer file are compared with the geometry and material properties of the dental ceramic blank. The process further includes mapping the specifications of the first computer file onto the dental ceramic blank to determine the volume of material to be removed, separating the volume of material to be removed into regions comprising degrees of accuracy and surface roughness. The regions are machined by rough machining, intermediate machining and/or fine machining steps. Each rough, intermediate and fine machining step comprises at least one tool path, machining parameters and tool selection. The tool path is calculated and converted into a series of commands in a second computer file. The second computer file, machining parameters and tool selection are provided to a milling machine.

In still further aspects, the dental ceramic blank may comprise lithium silicate having a strength in the range from approximately 80 to approximately 180 MPa and a fracture toughness in the range from approximately 0.7 to approximately 1.3 MPa·m$^{0.5}$. Additional strength ranges include approximately 90 to approximately 150 MPa. The flexural strength may be selected from flexural strength per ISO6872, 3-point bend strength, 4-point bend strength, biaxial flexure strength (also known as biaxial strength).

BRIEF DESCRIPTION OF THE DRAWINGS

FIG. 14a shows a perspective view of the grinding tool of FIG. 9.

FIG. 14b shows a cross-sectional view of the grinding tip of the grinding tool of FIG. 14a.

FIG. 14c shows a cross-sectional view of the grinding tool of FIG. 14a.

FIG. 15a shows a perspective view of the grinding tool of FIG. 10.

FIG. 15b shows a cross-sectional view of the grinding tip of the grinding tool of FIG. 15a.

FIG. 15c shows a cross-sectional view of the grinding tool of FIG. 15a.

FIG. 16b shows a cross-sectional view of the grinding tip of the grinding tool of FIG. 16a.

FIG. 16c shows a cross-sectional view of the grinding tool of FIG. 16a.

DETAILED DESCRIPTION OF THE INVENTION

Figure 1:
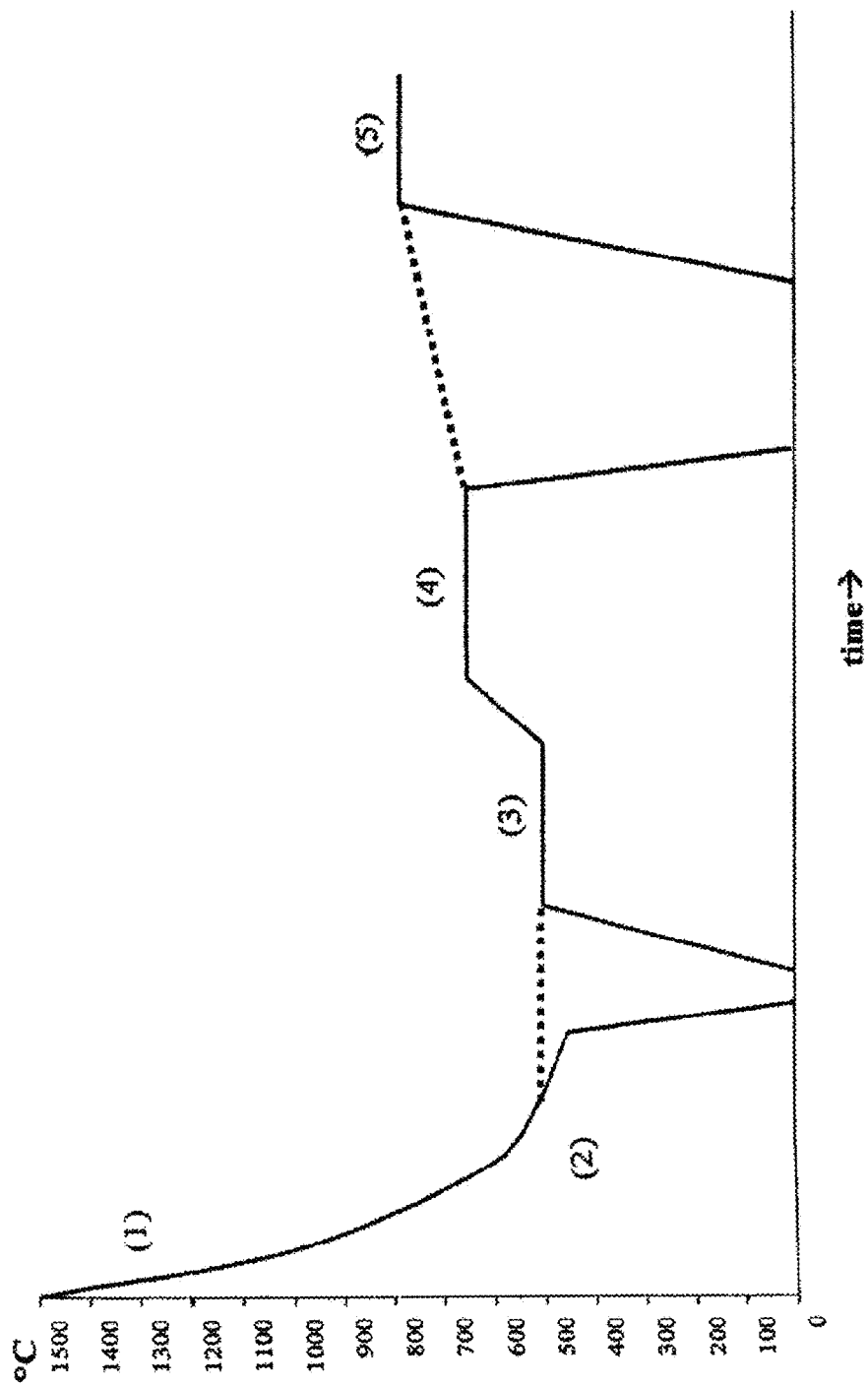
FIG. 1 shows a principle temperature profile of a process according to the invention starting from the melt via lithium metasilicate to lithium disilicate.

It should be mentioned that any references, including patents, patent applications and published articles that are cited herein are incorporated by reference in their entirety. Any word used herein in plural form may also include singular forms of the word and any word used in singular form herein may also include plural forms of the word.

It has surprisingly been shown that by using a starting glass of a very specific composition and a specific process it is possible to provide the glass ceramic according to the invention which has metastable lithium metasilicate ($Li_2SiO_3$) as main crystalline phase rather than lithium disilicate ($Li_2Si_2O_5$). This lithium metasilicate glass ceramic has a low strength and toughness and hence can be easily machined into the shape of even complicated dental restorations, but can after such machining be converted by a heat treatment into a lithium disilicate glass ceramic product with outstanding mechanical properties, excellent optical properties and very good chemical stability thereby undergoing only a very limited shrinkage.

The lithium silicate glass ceramic material according to the invention comprises the following components

| Component | Wt. % |
|---|---|
| $SiO_2$ | 64.0-73.0 |
| $Li_2O$ | 13.0-17.0 |
| $K_2O$ | 2.0-5.0 |
| $Al_2O_3$ | 0.5-5.0 |
| $P_2O_5$ | 2.0-5.0 | and comprises lithium metasilicate as main crystalline phase.

Another preferred embodiment of the present invention is formed by a silicate glass ceramic material as described above which is formed in a process which includes a step wherein lithium metasilicate as main crystalline phase is produced.

It is preferred that the lithium silicate material of the present invention further comprises the following additional components independently from each other

| Component | Wt. % |
|---|---|
| ZnO | 0.5-6.0, preferably 2.0-6.0 |
| $Na_2O$ | 0.0-2.0 |
| $Me^{II}O$ | 0.0-7.0, preferably 0.0-5.0 |
| $ZrO_2$ | 0.0-2.0 |
| colouring and fluorescent metal oxides | 0.5-7.5 | with $Me^{II}O$ being one or more members selected from the group consisting of CaO, BaO, SrO and MgO.

A lithium silicate material which comprises the following components, independently of one another, in the following amounts is particularly preferred:

| Component | Wt. % |
|---|---|
| $SiO_2$ | 65.0-70.0 |
| $Li_2O$ | 14.0-16.0 |
| $K_2O$ | 2.0-5.0 |
| $Al_2O_3$ | 1.0-5.0 |
| $P_2O_5$ | 2.0-5.0 |
| ZnO | 2.0-6.0 |
| $Na_2O$ | 0.1-2.0 |
| $Me^{II}O$ | 0.1-7.0, preferably 0.1-5.0 |
| $ZrO_2$ | 0.1-2.0 |
| coloring and fluorescent metal oxides | 0.5-3.5 | with $Me^{II}O$ being one or more members selected from the group consisting of CaO, BaO, SrO and MgO, and with the metal of the one or more coloring and fluorescent metal oxides being preferably selected from the group consisting of Ta, Tb, Y, La, Er, Pr, Ce, Ti, V, Fe and Mn.

The phrase " . . . independently from each other . . . " means that at least one of the preferred amounts is chosen and that it is therefore not necessary that all components are present in the preferred amounts.

As colouring components or fluorescent components for example oxides of f-elements may be used, i.e. the list of metals given above is not to be seen as terminal. The colouring or fluorescent components ensure that the colour of the final dental product matches that of the natural tooth material of the patient in question.

In the above composition $P_2O_5$ acts as a nucleation agent for the lithium metasilicate crystals and a concentration of at least 2 wt % is required for the necessary nucleation. Instead of $P_2O_5$, other nucleation agents are also possible, e.g. compounds of the elements Pt, Ag, Cu and W.

In addition to the components mentioned above the glass ceramic may further comprise additional components to enhance the glass technical processability. Such additional components may therefore be in particular compounds such as $B_2O_3$ and F which in general amount to 0 to 5.0% by weight.

A lithium silicate material as described above is particularly preferred which comprises 67.0 to 70.0 wt % of $SiO_2$.

It has surprisingly been shown that a specific volume portion of lithium metal silicate should be present to achieve excellent processing properties. Thus, it is further preferred that the lithium metasilicate crystalline phase forms 20 to 50 vol % and in particular 30 to 40 vol % of the lithium silicate material. Such a part of the volume leads to the crystals being present rather remote from each other and hence avoids a too high strength of the lithium silicate material.

The lithium metasilicate crystals are preferably of lamellar or platelet form. This leads to a very good machinability of the lithium silicate material without use of high energy and without uncontrolled breaking. The latter aspect of uncontrolled breaking is for example known from glasses which are generally unsuitable for machining. It is assumed that the preferred morphology of the lithium metasilicate crystals is also responsible for the surprisingly high edge strength of products, e.g. complicated dental restorations, can be made from the lithium silicate material according to the invention.

The lithium silicate material according to the invention preferably is in the form of a blank. The blank usually takes the form of a small cylinder or a rectangular block. The exact form depends on the specific apparatus used for the desired computer-aided machining of the blank.

After the machining, the lithium silicate material according to the invention has preferably the shape of a dental restoration, such as an inlay, an onlay, a bridge, an abutment, a facing, a veneer, a facet, a crown, a partial crown, a framework or a coping.

A lithium disilicate material which is formed in a process which includes a step wherein a phase comprising primarily crystalline lithium metasilicate is produced, the lithium metasilicate being subsequently converted to lithium disilicate forms a preferred embodiment of the invention.

A dental product made from lithium disilicate, said lithium disilicate being formed in a process which includes a step wherein a phase comprising primarily crystalline lithium metasilicate is produced, the lithium metasilicate being subsequently converted to lithium disilicate forms another preferred embodiment of the present invention.

A blank of lithium silicate glass ceramic material according to the invention is preferably prepared by a process which comprises (a) producing a melt of a starting glass containing the initial components $SiO_2$, $Li_2O$, $K_2O$, $Al_2O_3$ and $P_2O_5$ as the main components, (b) pouring the melt of the starting glass into a mould to form a starting glass blank and cooling the glass blank to room temperature, (c) subjecting the starting glass blank to a first heat treatment at a first temperature to give a glass product which contains nuclei suitable for forming lithium metasilicate crystals, (d) subjecting the glass product of step (c) to a second heat treatment at a second temperature which is higher than the first temperature to obtain the lithium silicate blank with lithium metasilicate crystals as the main crystalline phase.

A process as described above, wherein the starting glass of step (a) further comprises ZnO, $Na_2O$, $Me^{II}O$, $ZrO_2$, and coloring and fluorescent metal oxides, with $Me^{II}O$ being one or more members selected from the group consisting of CaO, BaO, SrO and MgO is preferred.

A process as described above, wherein the starting glass of step (a) comprises the following initial components, independently of one another, in the following amounts

| Component | Wt. % |
|---|---|
| $SiO_2$ | 65.0-70.0 |
| $Li_2O$ | 14.0-16.0 |
| $K_2O$ | 2.0-5.0 |
| $Al_2O_3$ | 1.0-5.0 |
| $P_2O_5$ | 2.0-5.0 |
| ZnO | 2.0-6.0 |
| $Na_2O$ | 0.1-2.0 |
| $Me^{II}O$ | 0.1-7.0, preferably 0.1-5.0 |
| $ZrO_2$ | 0.1-2.0 |
| coloring and fluorescent metal oxides | 0.5-3.5 | with $Me^{II}O$ being one or more members selected from the group consisting of CaO, BaO, SrO and MgO and with the metal(s) of the one or more coloring and fluorescent metal oxides being preferably selected from the group consisting of Ta, Tb, Y, La, Er, Pr, Ce, Ti, V, Fe and Mn is even more preferred.

In step (a), a melt of a starting glass is produced which contains the components of the glass ceramic. For this purpose a corresponding mixture of suitable starting materials, such as carbonates, oxides, and phosphates, is prepared and heated to temperatures of, in particular 1300 to 1600° C., for 2 to 10 hours. In order to obtain a particularly high degree of homogeneity, the glass melt obtained may be poured into water to form glass granules and the glass granules obtained are melted again.

In step (b), the melt of the starting glass is poured into a corresponding mould, e.g. a steel mould, and cooled to room temperature to give a glass product.

The cooling is preferably conducted in a controlled manner so as to allow a relaxation of the glass and to prevent stresses in the structure associated with rapid temperature changes. As a rule, the melt is therefore poured into preheated moulds, e.g. of a temperature of about 400° C. Subsequently, the product can slowly be cooled in a furnace to room temperature.

In step (c) the starting glass product is subjected to a first heat treatment at a first temperature to cause formation of nuclei for lithium metasilicate crystals. Preferably, this first heat treatment involves a heating of the glass product for a period of 5 minutes to 1 hour at a first temperature of 450 to 550° C. In some cases it is convenient to combine step b) and step c) in order to relax the glass article and nucleate the lithium metasilicate crystals in one single heat treatment therefore a process as described above, wherein step (c) is replaced by modifying step (b) such that during the cooling process a temperature of about 450 to 550° C. is held for a period of about 5 minutes to 50 minutes to produce the glass product which contains nuclei suitable for formation of the lithium metasilicate crystals during step (b) forms a preferred embodiment of the invention.

A process as described above, wherein in step (c) the first heat treatment comprises heating the starting glass blank to a temperature of about 450 to 550° C. for a period of about 5 minutes to 1 hour forms another preferred embodiment of the invention.

Subsequently, the glass product comprising the desired nuclei is cooled to room temperature.

In the subsequent step (d), the glass product having the desired nuclei of $Li_2SiO_3$ is subjected to a second heat treatment at a second temperature which is higher than the first temperature. This second heat treatment results in the desired formation of lithium metasilicate crystals as predominant and preferably as only crystalline phase and therefore gives the lithium metasilicate glass ceramic according to the invention. Preferably, this second heat treatment of step (d) comprises heating the glass product which contains nuclei suitable for formation of lithium silicate crystals to a second temperature of about 600 to 700° C. for a period of about 10 to 30 minutes.

The principle temperature profile of such a process is exemplified in FIG. 1. Already starting from the melt (1), i.e. at the end of step a) the temperature decreases for relaxation of the product in a temperature range of 500 to 450° C. (2). The temperature can then be brought to room temperature (solid line), step b), and afterwards be brought to a temperature of about 450 to 550° C. or can be kept in the temperature range of 450 to 500° C. (dotted line). In the region that is labeled with (3), step c), nucleation occurs at a temperature of 450 to 550° C. and is influenced by $P_2O_5$. Then, the glass material can be heated directly to a temperature in the range of 600 to 700° C. and kept at said temperature (4) during which time lithium metasilicate forms, step d). Subsequently the material can be cooled down (solid line) to e.g. about room temperature for grinding, milling or CAD-CAM processing and can afterwards be brought to a temperature of about 700 to 950° C. or can directly be brought to 700 to 950° C. (dotted line) at which temperature (5) the second crystallization occurs forming the lithium disilicate and where additional heat treatment or hot pressing can be undertaken.

Depending on the specific composition of a selected starting glass, it is possible for the skilled person by means of differential scanning calorimetry (DSC) and x-ray diffraction analyses to determine suitable conditions in steps (c) and (d) to result in materials having the desired morphology and size of the crystals of lithium metasilicate. To further illustrate this process FIGS. 2 to 5 together with Tables I and II in the example section indicate how the relevant data were obtained for example 13 using said measurements and are therefore obtainable in general. Moreover, these analyses allow also the identification of conditions avoiding or limiting the formation of undesirable other crystalline phases, such as of the high-strength lithium disilicate, or of cristobalite and lithium phosphate.

Subsequent to step (d), it is preferred to shape the obtained glass ceramic. This is preferably effected by step (e), wherein the lithium metasilicate glass ceramic is machined to a glass ceramic product of the desired shape, in particular the shape of a dental restoration. The machining is preferably carried out by trimming or milling. It is further preferred that the machining is controlled by a computer, in particular by using CAD/CAM-based milling devices. This allows a so-called chair-side treatment of the patient by the dentist.

It is a particular advantage of the glass ceramic according to the invention that it can be shaped by machining without the undue wear of the tools observed with the tough and high-strength prior art materials. This is in particular shown by the easy possibility to polish and trim the glass ceramics according to the invention. Such polishing and trimming processes therefore require less energy and less time to prepare an acceptable product having the form of even very complicated dental restorations.

Lithium disilicate dental restorations can be produced in many different ways. Commonly used by dental technicians are the CAD/CAM and the hot pressing technique. Dentists can use a CAD/CAM method (Cerec 2®, Cerec 3®) to produce chair-side an all ceramic lithium disilicate restoration. The final result is always a dental restoration with lithium disilicate as the main crystalline phase. For this purpose, the blank can be a lithium metasilicate glass ceramic according to the invention. The glass ceramic according to the invention can therefore be processed in both ways, by CAD/CAM or by hot-pressing, which is very advantageous for the user.

It is also possible to use for these purposes a corresponding lithium silicate glass which comprises nuclei suitable for formation of lithium metasilicate crystals. This glass is a precursor of the lithium metasilicate glass ceramic of the invention. The invention is also directed to such a glass. It is obtainable by the above process in step (c).

For manufacturing a dental restoration by the hot pressing technique a lithium silicate glass ingot having nuclei for lithium metasilicate is subjected to a heat treatment of about 700 to 1200° C. to convert it into a viscous state. The heat treatment will be conducted in a special furnace (EP 500®, EP 600®, Ivoclar Vivadent AG). The ingot is embedded in a special investment material. During the heat treatment the ingot will be crystallized. The main crystal phase is then lithium disilicate. The viscous glass ceramic flows under a pressure of 1 to 4 MPa into the cavity of the investment material to obtain the desired shape of the dental restoration. After cooling the investment mould to room temperature the lithium disilicate restoration can be divested by sand blasting. The framework can be further coated with a glass or a glass ceramic by sintering or hot pressing technique to get the finalized dental restoration with natural aesthetics.

An ingot which comprises the lithium silicate glass ceramic according to the invention is subjected to a heat treatment of about 700 to 1200° C. to convert it into a viscous state. The heat treatment will be conducted in a special furnace (EP 500®, EP 600®, Ivoclar Vivadent AG). The glass ceramic ingot is embedded in a special investment material. During the heat treatment the glass ceramic will be further crystallized. The main crystal phase is then lithium disilicate. The viscous glass ceramic flows under a pressure of 1 to 4 MPa into the cavity of the investment material to obtain the desired shape of the dental restoration. After cooling the investment mould to room temperature the lithium disilicate restoration can be divested by sand blasting. The framework can be further coated with a glass or a glass ceramic by sintering or hot pressing technique to get the finalized dental restoration with natural aesthetics.

For manufacturing a dental restoration by the CAD/CAM technique the lithium silicate or the lithium metasilicate blocks with lithium disilicate as possible minor crystalline phase having a strength of about 80 to 150 MPa can be easily machined in a CAM unit like Cerec 2® or Cerec 3® (Sirona, Germany). Larger milling machines such as DCS Precimill® (DCS, Switzerland) are also suitable. The block is therefore positioned in the grinding chamber by a fixed or integrated holder. The CAD construction of the dental restoration is done by a scanning process or an optical camera in combination with a software tool. The milling process needs for one unit 10 to 15 minutes. Copy milling units such as Celay® (Celay, Switzerland) are also suitable for machining the blocks. First, a 1:1 copy of the desired restoration is fabricated in hard wax. The wax model is then mechanically scanned and 1:1 mechanically transmitted to the grinding tool. The grinding process is therefore not controlled by a computer. The milled dental restoration has to be subjected to a heat treatment to get the desired lithium disilicate glass ceramic with high strength and tooth like color. The heat treatment is conducted in the range of 700 to 900° C. for a period of about 5 to 30 minutes. The framework can be further coated with a glass or a glass ceramic by sintering or hot pressing technique to get the finalized dental restoration with natural aesthetics.

Blocks with lithium disilicate as main crystalline phase can only be grinded in a large milling machine such as DCS Precimill® (DCS, Switzerland) due to the high strength and toughness of the glass ceramic. The block is therefore positioned in the grinding chamber by a fixed metal holder. The CAD construction of the dental restoration is done by a scanning process in combination with a software tool. An additional heat treatment in the range of 700 to 900° C. could be conducted in order to close surface flaws which were induced by the grinding process. The framework can be further coated with a glass or a glass ceramic by sintering or hot pressing technique to get the finalized dental restoration with natural aesthetics.

It has further been shown that the easily machinable lithium metasilicate glass ceramic according to the invention can be converted into a lithium disilicate glass ceramic product by a further heat treatment. The obtained lithium disilicate glass ceramic has not only excellent mechanical properties, such as high strength, but also displays other properties required for a material for dental restorations.

Thus, the invention also relates to a process for preparing a lithium disilicate glass ceramic product, which comprises (f) subjecting the Lithium metasilicate glass ceramic according to the invention to a third heat treatment to convert lithium metasilicate crystals to lithium disilicate crystals.

In this step (f), a conversion of the metastable lithium metasilicate crystals to lithium disilicate crystals is effected. Preferably, this third heat treatment involves a complete conversion into lithium disilicate crystals and it is preferably carried out by heating at 700 to 950° C. for 5 to 30 minutes. The suitable conditions for a given glass ceramic can be ascertained by conducting XRD analyses at different temperatures.

It was also found out that the conversion to a lithium disilicate glass ceramic is associated with only a very small linear shrinkage of only about 0.2 to 0.3%, which is almost negligible in comparison to a linear shrinkage of up to 30% when sintering ceramics.

A process as described above, wherein the lithium silicate blank has a biaxial strength of at least 90 MPa and a fracture toughness of at least 0.8 MPam$^{0.5}$ is preferred.

A process as described above, wherein the starting glass blank of step (b), the glass product containing nuclei suitable for forming lithium metasilicate of step (c), or the lithium silicate blank with lithium metasilicate as the main crystalline phase of step (d) is shaped to a desired geometry by machining or by hot pressing to form a shaped lithium silicate product is also preferred.

Such a process, wherein the shaped lithium silicate blank is a dental restoration is more preferred and a process wherein the dental restoration is an inlay, an onlay, a bridge, an abutment, a facing, a veneer, a facet, a crown, a partial crown, a framework or a coping is even more preferred.

A process as described above, wherein the machining is performed by grinding or milling forms a preferred embodiment of the invention, whereby a process wherein the machining is controlled by a computer is even more preferred.

A process as described above but further comprising subjecting the shaped lithium silicate product to a third heat treatment at a third temperature of about 700 to 950° C. for a period of about 5 to 30 minutes is another aspect of the present invention and said process is particularly preferred when the lithium silicate product subjected to the third heat treatment comprises lithium metasilicate as the main crystalline phase, and wherein the third heat treatment converts the lithium metasilicate crystals to lithium disilicate crystals as the main crystalline phase of the dental restoration.

A process as described above wherein the lithium silicate product subjected to the third heat treatment comprises the glass product containing nuclei suitable for forming lithium metasilicate crystals, and wherein lithium disilicate crystals are crystallized directly from the nuclei suitable for forming lithium metasilicate crystals is also preferred.

Another preferred embodiment of the present invention is a process as described above, wherein the shrinkage that occurs during the third heat treatment is less than 0.5%, preferably less than 0.3%, by volume.

A process as described above which comprises shaping of a lithium silicate material to the desired geometry by hot pressing to produce the dental restoration is also an object of the invention, with a process for manufacturing a dental restoration as described above being preferred wherein the hot pressing comprises subjecting the lithium silicate material to a heat treatment at a temperature of about 500 to 1200° C. to convert the lithium silicate material into a viscous state and pressing the viscous lithium silicate material under a pressure of about 1 to 4 MPa into a mould or dye to obtain the dental restoration with a desired geometry.

A process as described above, wherein the lithium silicate material subjected to the heat treatment and pressing comprises lithium metasilicate crystals which are converted into lithium disilicate crystals during the heat treatment and pressing is more preferred.

A further preferred embodiment of the present invention is formed by a process as described above which comprises an increasing of strength and fracture toughness of the lithium silicate material.

A process for the manufacture of a dental restoration as described above is preferred, wherein the dental restoration has a biaxial strength of at least 250 MPa and a fracture toughness of at least 1.5 MPam$^{0.5}$.

A process for the manufacture of a dental restoration as described above further comprising finishing the dental restoration to obtain a natural appearance is preferred.

Same is true for a process as described above, wherein the finishing step comprises applying a coating to the dental restoration by layering with powdered materials or by hot pressing a coating material onto the unfinished dental restoration.

A process as described above wherein the third heat treatment occurs during a firing of the layering materials or the hot pressing of the coating material onto unfinished the dental restoration is even more preferred.

Thus, a product is finally obtained which has all the beneficial mechanical, optical and stability properties making lithium disilicate ceramics attractive for use as dental restorative materials. However, these properties are achieved without the disadvantages of the conventional materials when shaped by using a CAD/CAM based process, in particular the undue wear of the milling and trimming tools.

Consequently, the invention also relates to a lithium disilicate glass ceramic product which is obtainable by the above process for its preparation and has lithium disilicate as main crystalline phase. Preferably, the lithium disilicate glass ceramic product according to the invention is in the form of a dental restoration.

It is further preferred that in the lithium disilicate glass ceramic the lithium disilicate crystals form 60 to 80% by volume of the glass ceramic.

The conversion of the lithium metasilicate glass ceramic according to the invention to a lithium disilicate glass ceramic product is associated with a surprisingly high increase in strength by a factor of up to about 4. Typically, the lithium metasilicate glass ceramic of the invention has a strength of about 100 MPa, and the conversion leads to a lithium disilicate glass ceramic having a strength of more than 400 MPa (measured as biaxial strength).

The invention is also directed to a lithium silicate blank as described above, wherein the blank is combined with a holder, stem or retainer to fit into the milling machine or an adapter that fits into the milling machine.

A lithium silicate blank as described above, wherein the holder is from a different material from the blank forms one embodiment of the invention.

A lithium silicate material blank as described above, wherein the holder is made from an alloy, from a metal, from a glass ceramic or from a ceramic forms a preferred embodiment of the invention.

A lithium silicate blank as described above, wherein the holder is made from the same material as the blank and is integral with the blank is another embodiment of the invention.

A lithium silicate blank as described above, wherein the blank is labeled with information is another preferred embodiment.

Same is true for a lithium silicate blank as described above, wherein the information on the blank comprises the material, the size and the type of the shape, which is to be machined from the blank.

Another aspect of the present invention is directed to a method for manufacturing a lithium silicate restoration comprising preparing lithium silicate ingots or blanks as described above, and thereafter overlaying a dental restoration with the lithium silicate material by heat (hot) pressing over the framework material or alternatively machining (grinding or milling) a shape of overlay from the blank with all the necessary occlusal and cervical details and bonding the machined lithium silicate overlay to a framework material.

A method for manufacturing a dental restoration as described above wherein a dental framework is coated by hot pressing the lithium silicate blank onto the dental framework is one of the preferred embodiments. Other preferred methods comprise milling, staining/glazing and bonding overlay rather than conventional layering or heat pressing as described in WO 2007/028787 A1 by Schweiger et al. and also US Patent Applications 2006/0257823 and 2006/0257824 by Pfeiffer, all of which are hereby incorporated by reference herein in their entirety.

A method for manufacturing a dental restoration as described above, wherein the dental framework is a crown, a partial crown, a bridge, a coping, a veneer, a facing or an abutment is more preferred and such a method, wherein the dental framework is made from a metal, an alloy, a ceramic or a glass ceramic is even more preferred.

A method for manufacturing a dental restoration as described above, wherein the framework ceramic comprises zirconium oxide (zirconia), aluminum oxide (alumina), a zirconium mix oxide, an aluminium mix oxide, an alumina toughened zirconia, a zirconia toughened alumina or a combination thereof forms a particularly preferred embodiment of the invention.

A method for manufacturing a dental restoration as described above wherein the lithium silicate blank which is coated onto the framework comprises lithium metasilicate crystals which are converted to lithium disilicate crystals, or the lithium silicate blank comprises nuclei suitable for forming lithium metasilicate crystals which crystallize as lithium disilicate crystals during the hot pressing of the lithium silicate blank onto the dental framework is another preferred object of the invention.

The invention is explained in more detail below on the basis of the following nonlimiting Examples.

EXAMPLES

Examples 1 to 18 (Invention), 19 to 20 (Comparison) and 21 to 23 (Invention)

A total of 18 different lithium metasilicate glass ceramic products according to the invention as well as two ceramics for comparison with the chemical compositions given in Table III were prepared by carrying out stages (a) to (d) of the process described above and finally converted to lithium disilicate glass ceramic products by step (e) of the process described above:

For this purpose samples of the corresponding starting glasses were melted in a platinum-rhodium crucible at a temperature of 1500° C. and for a period of 3 hours (a).

The glass melts obtained were then poured into steel moulds which were preheated to 300° C. After 1 minute the glass blanks were transferred into a furnace which was preheated to a temperature between 450 and 550° C. The exact values, KB T [° C.] and KB t [min], are given for each sample in Table III. After this relaxation and nucleation process (b and c) the blocks were allowed to cool to room temperature. The nucleated samples were homogeneous and transparent.

The glass blanks, which contained nuclei for the crystallization, were then subjected to step (d), i.e. the second heat treatment, to crystallize lithium metasilicate, which means that the glass blanks were exposed to a temperature of about 650° C. for a period of about 20 minutes, except example 3, which was crystallized at 600° C.

The course of the crystallization was investigated by DSC-measurement and the resulting crystal phases were analyzed by XRD to identify the ideal conditions for this heat treatment. "Ideal conditions" in the sense of the present invention are present in case the two crystallization peaks of the meta- and the disilicate phase respectively are differing to such an extend that in the production process a neat differentiation can be implemented, i.e. when heating a sample to the first crystallization temperature it has to be secured that when reaching the desired temperature within the sample the temperature at the outer regions of the sample does not reach the second crystallization temperature, i.e. the bigger the temperature difference of the first and the second crystallization temperature is the bigger the sample mass can be.

Figure 2:
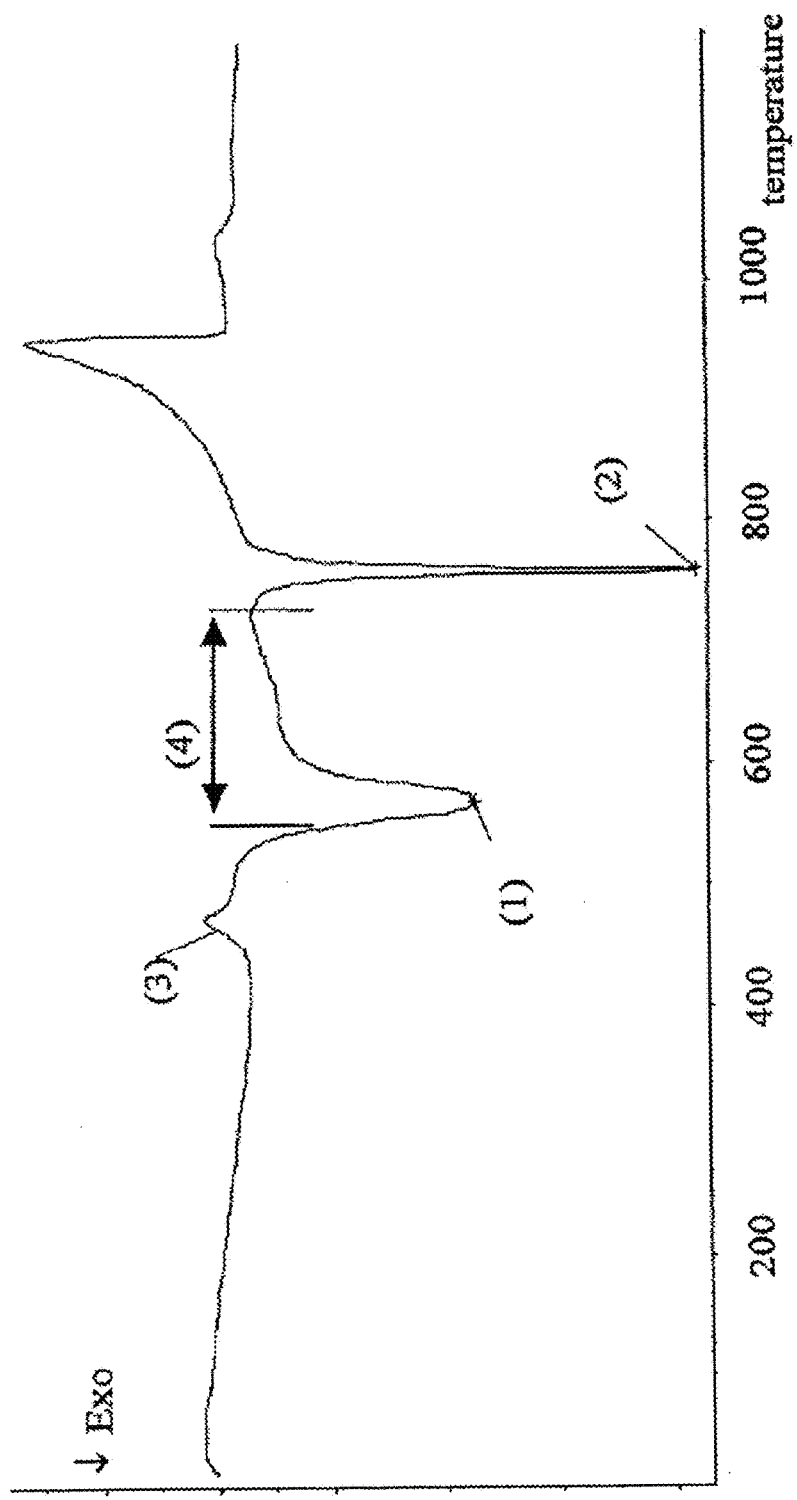
FIG. 2 shows a DSC-plot of a lithium silicate material according to example 13.

To further illustrate the process FIG. 2 shows a DSC-plot of one of the examples, example 13, a quenched and powdered glass sample, which was heated with a heating rate of 10 K/min. The crystallisation of lithium metasilicate (1), the crystallisation of lithium disilicate (2) as well as the glass transition temperature (3) and the temperature range (4) for the first crystallisation are clearly visible from said DSC-plot.

Figure 3:
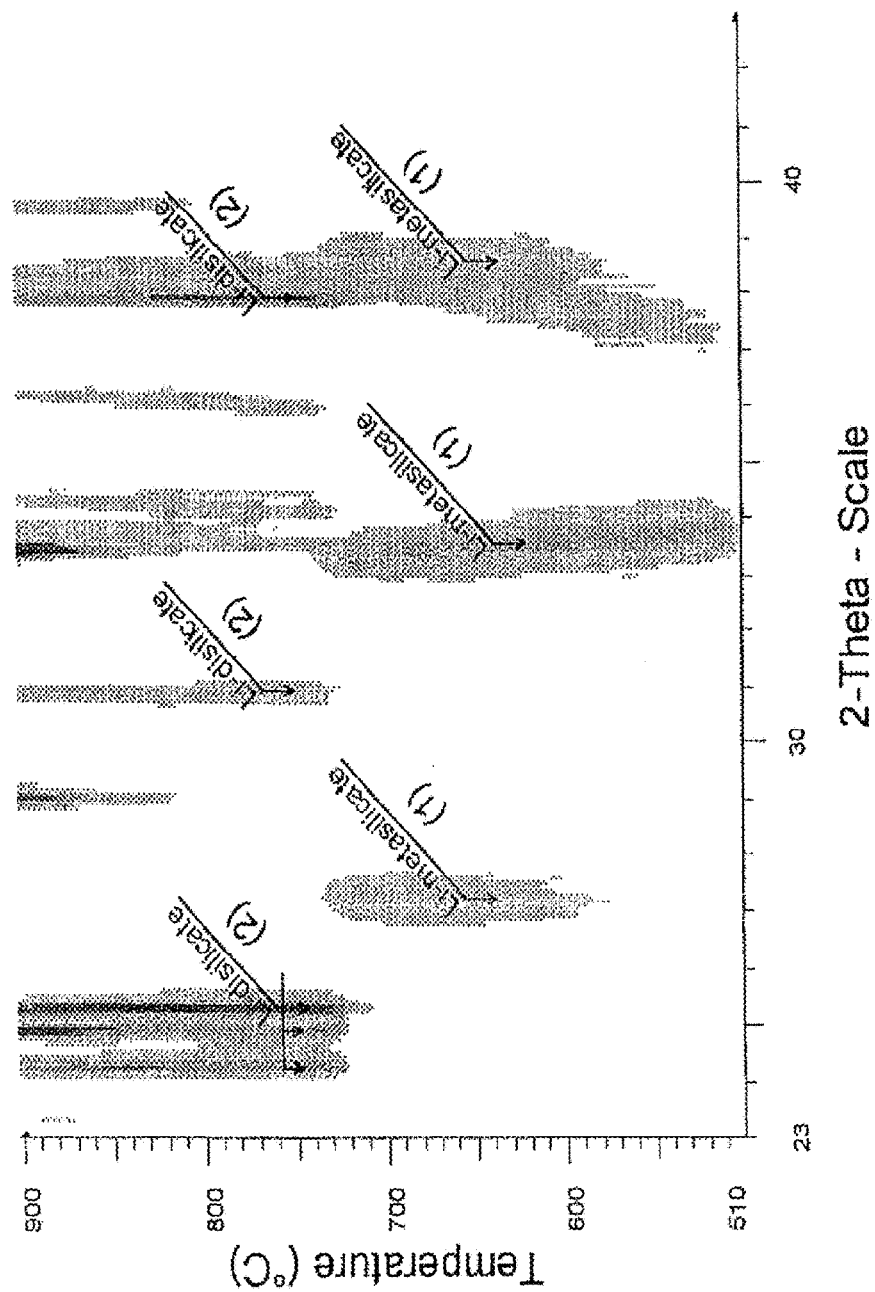
FIG. 3 shows a high temperature XRD of a lithium silicate material according to example 13, in form of a bulk glass sample.

Also an example for the analysis of phase development by high temperature XRD from the same example 13 is given. FIG. 3 therefore shows the measurement of a bulk glass sample at a constant heating rate of 2 K/min. It can be recognized from said measurement that in this case the crystallisation of the lithium metasilicate (1) occurs at a temperature of 510° C. and that in this case the resolution of the lithium metasilicate and the crystallization of the lithium disilicate (2) occur at a temperature of 730° C.

Figure 4:
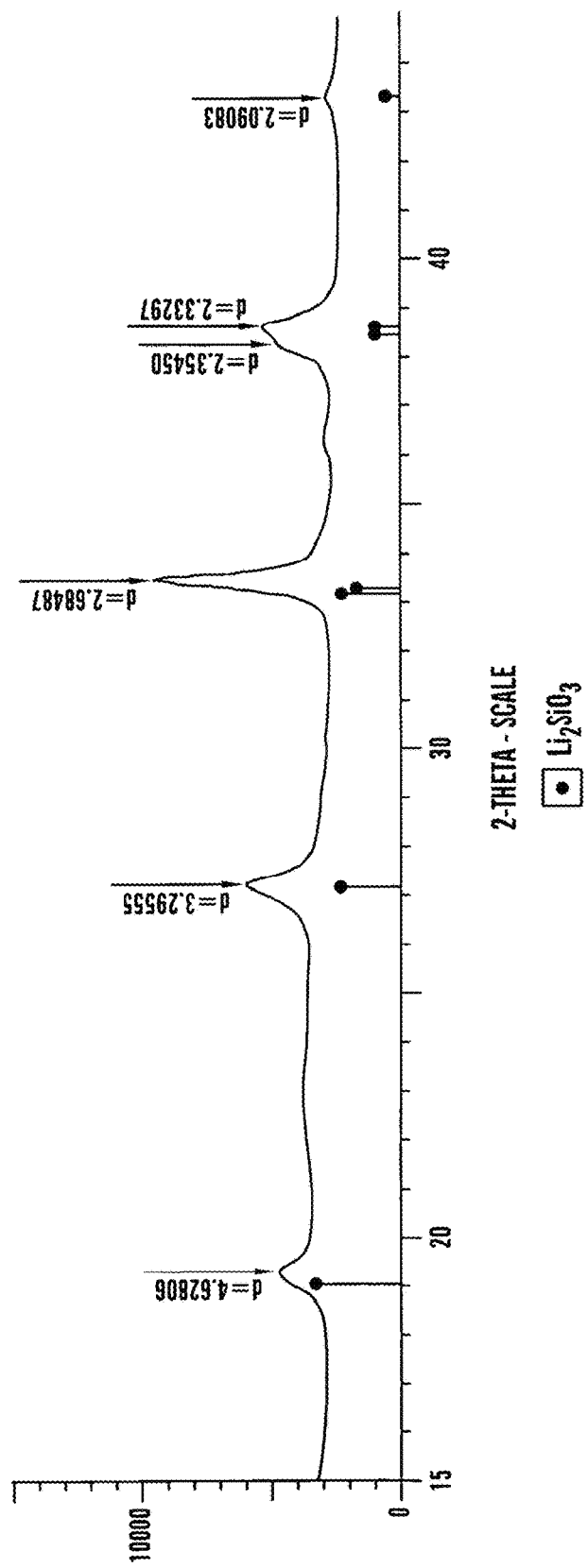
FIG. 4 shows an XRD for phase analysis of a lithium silicate material according to example 13 after nucleation and first crystallization.

FIG. 4 represents a phase analysis by XRD of example 13 after nucleation at 500° C. for 7 min and first crystallisation at 650° C. and 20 min.

The corresponding data are summarized In Table I:

TABLE I

| 1<br>d-spacing in 0.1 nm<br>of scan | 2<br>d-spacing in 0.1 nm<br>of pattern | 3<br>Index |
|---|---|---|
| 4.628 | 4.690 | LS 020 |
| 3.296 | 3.301 | LS 111 |
|  | 2.708 | LS 130 |

TABLE I-continued

| 1<br>d-spacing in 0.1 nm<br>of scan | 2<br>d-spacing in 0.1 nm<br>of pattern | 3<br>Index |
|---|---|---|
| 2.685 | 2.700 | LS 200 |
| 2.355 | 2.342 | LS 131 |
| 2.333 | 2.331 | LS 002 |

Figure 5:
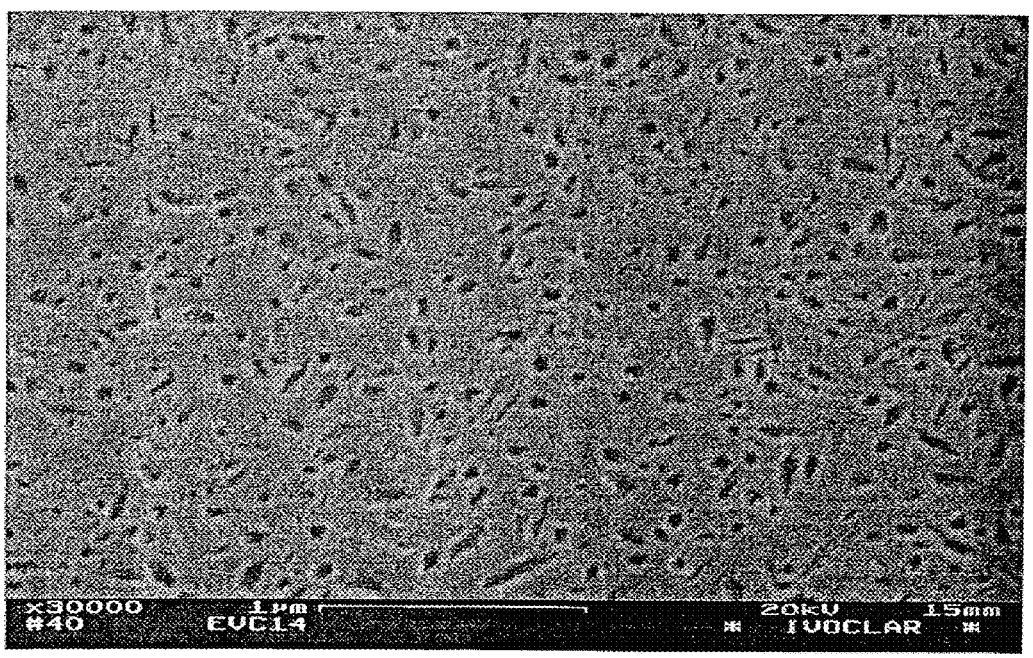
FIG. 5 shows an SEM-micrograph, back scattered electrons, of a lithium silicate material according to example 13 after nucleation and first crystallization.

FIG. 5 shows an SEM-micrograph, backscattered electrons, of the same example having the same thermal history, with the surface being etched with 1% HF for 8 s. Clearly visible are holes that show former lithium metasilicate crystals.

The resulting blocks were now ready for step (e), which means shaping the lithium metasilicate glass ceramic to the desired shape, either by saw cutting, or by milling it in a CAD-CAM milling machine (i.e. CEREC 3®). The obtained lithium metasilicate glass ceramic blanks were analyzed for their machinability and their edge strength. 10 discs were cut from a rod with 12 mm diameter for biaxial strength measurements. The results of these analyses are given in Table IV. Ten more discs were prepared and subjected to a third heat treatment (f).

In case the blanks contain colouring and fluorescent oxides the blocks in the state of the metasilicate appear to have a reddish or bluish colour. This effect vanishes when the disilicate phase forms and the blanks turn to the colour that is desired.

Finally, the lithium metasilicate glass ceramic blanks were subjected to a second crystallization, step (f), at 850° C. for 10 min, except example 3 which was crystallized at 830° C., i.e. the third heat treatment which is in general performed at temperatures of 700 to 950° C., preferably 820 to 880° C. and for a period of 5 to 30 minutes, preferably 5 to 20 minutes, to convert the lithium metasilicate into lithium disilicate.

Figure 6:
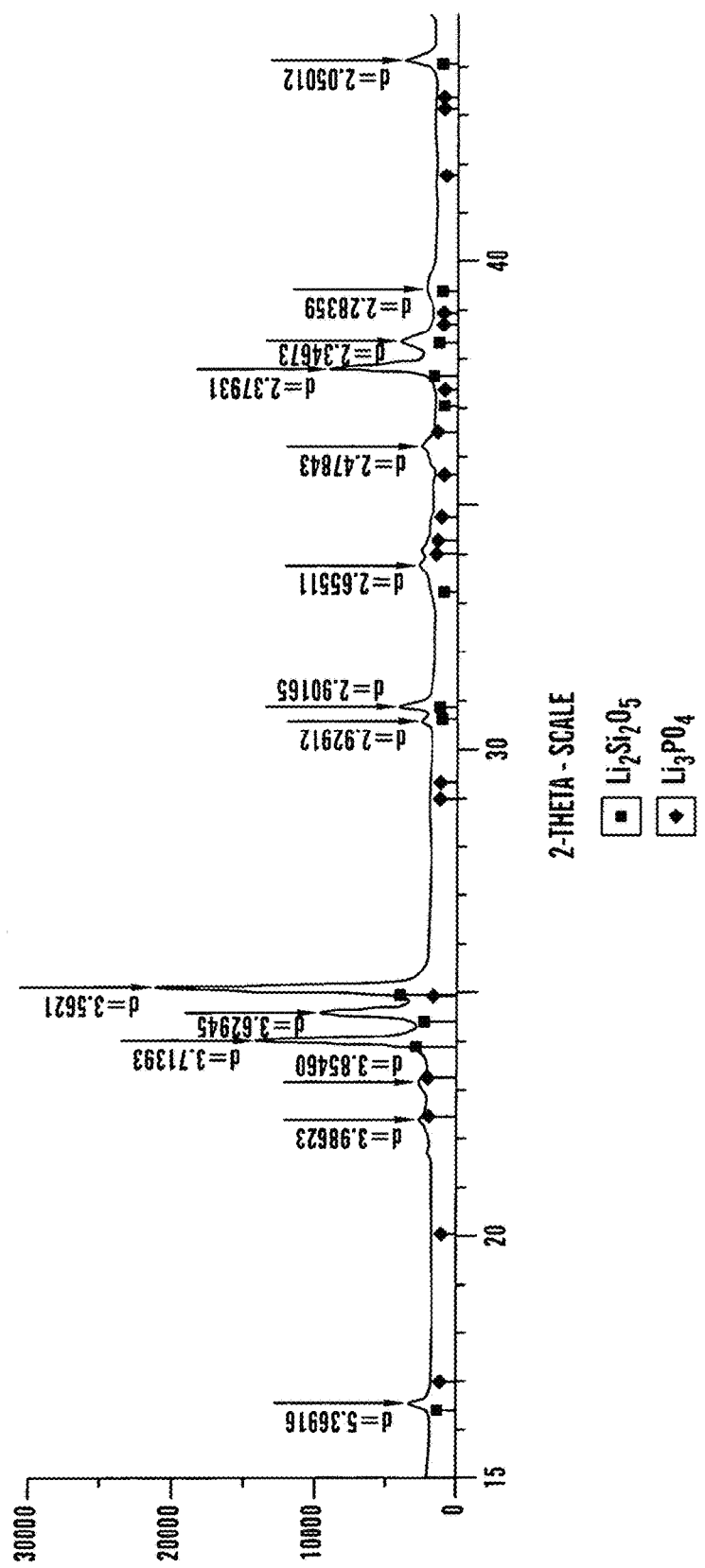
FIG. 6 shows an XRD for phase analysis of a lithium silicate material according to example 13 which was subjected to nucleation, first crystallization and second crystallization conditions.

The obtained products were analyzed for their crystal phases. To further illustrate the procedure the phase analysis for example 13 after nucleation at 500° C. for 7 min, first crystallization at 650° C. for 20 min and second crystallization at 850° C. for 10 is shown in FIG. 6. The corresponding data are summarized in Table II.

TABLE II

| 1<br>d-spacing in 0.1 nm<br>of scan | 2<br>d-spacing in 0.1 nm<br>of pattern | 3<br>Index |
|---|---|---|
| 5.369 | 5.420 | LS2 110 |
| 3.986 | 3.978 | LP 120 |
| 3.855 | 3.834 | LP 101 |
| 3.714 | 3.737 | LS2 130 |
| 3.629 | 3.655 | LS2 040 |
| 3.562 | 3.581 | LS2 111 |
| 2.929 | 2.930 | LS2 131 |
| 2.901 | 2.908 | LS2 200 |
| 2.379 | 2.388 | LS2 002 |
| 2.346 | 2.35 | LS2 221 |
| 2.283 | 2.29 | LS2 151 |
| 2.050 | 2.054 | LS2 241 |

Figure 7:
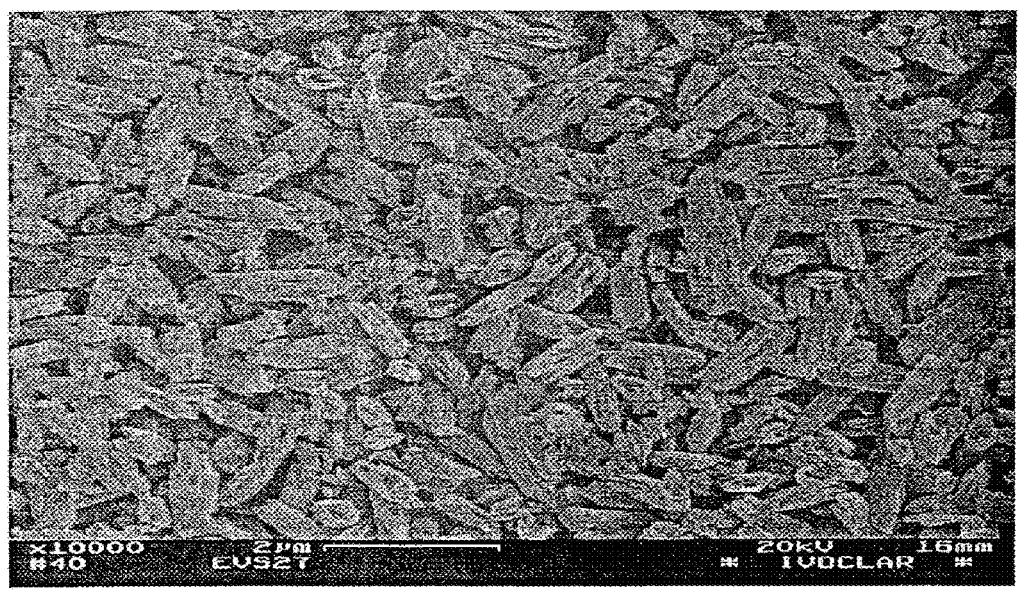
FIG. 7 shows an SEM-micrograph, back scattered electrons, of a lithium silicate material according to example 13 which was subjected to nucleation, first crystallization and second crystallization conditions and has an etched surface.

FIG. 7 shows an SEM-micrograph, backscattered electrons, of the same example having the same thermal history, with the surface being etched with 3% HF for 30 s leading to the glassy phase being etched out and leaving the lithium disilicate crystals.

In addition to the analysis in respect to crystal phases the samples were also analyzed in respect to their biaxial strength and chemical durability. Furthermore, their translucence was assessed. The results are also given in Table IV.

In table IV, the detected crystalline phases are designated as follows:
LS—lithium metasilicate
LS2—lithium disilicate
LP—lithium phosphate,
with the main phase being marked in bold type.

To gain information about the machinability tests were performed on a Cerec® 3, with new tools being used for each test. A 'Lego®-Minicube' served as a model which had to be milled from all compositions that were subjected to this test and from a leucite-enforced glass ceramic of the name ProCAD® from Ivoclar Vivadent AG. The operating sequence was as follows: First a blank of ProCAD@ was milled, then a blank of the ceramic to be tested was milled and after that again a ProCAD® blank was milled. The machinability was rendered "very good" in case the time that was required to mill the blank of the ceramic to be tested was below 95% of the time that was required to mill the ProCAD® blank. Times in the range of 95 to 105% of said time led to the mark "good" for the machinability, times in the range of 105 to 115% to "acceptable" and times above 115% to "poor". The medium time required for the milling process was 14.0 minutes.

To compare the machinability of the test samples with another glass ceramic a blank made according to the composition disclosed in DE 197 50 794 was prepared and subjected to the test described above. After 15 minutes the test was abandoned since only about 10% of the volume to be milled was already milled and the tools used for milling were already worn out, something that did not happen with any of the test samples.

The edge strength was determined as follows:
With a milling unit (CEREC 3®) blanks were milled to result in Lego-minicubes. With a 1.6 mm cylindrical diamond cutter blind holes were milled. The quality of said blind holes was determined by comparing the area of the broken out edges with those of a reference sample (Pro-CAD®). The relation of the area of the broken out edges to the area of the blind bore is an allocation for the edge strength.

An edge strength is considered to be "very good" in case the relation of said areas is smaller than that of the reference, it is considered to be "good" in case the relations are about the same and it is considered to be "acceptable" in case the area is bigger than 110% of the reference sample.

The chemical durability was determined according to ISO 6872, i.e. as loss of mass after 16 h in 4% acetic acid at 80° C.

"Good" means that the solubility according to said method is below 100 pg/cm$^2$.

The strength was measured as biaxial strength according to ISO 6872 or as 3 point bending strength according to EN 843-1:

Bars of 12 mm diameter were casted and crystallized once. From these bars 20 discs with a thickness of 1, 2 mm each were sawn. 10 of these discs were then smoothed and the surfaces of the discs were polished using SiC-paper of grain size 1000. Biaxial strength was measured as is disclosed in ISO 6872. The other 10 discs were crystallized a second time at 800 to 900° C. to give the lithium disilicate phase. These solidified samples were smoothed on both sides and the surfaces were polished using SiC-paper of grain size 1000. Biaxial strength was then measured according to ISO 6872.

By comparison bending strength was measured on bars with dimensions of 25*3.5*3.0 mm were sawn out of a block of the lithium metasilicate glass ceramic. These bars were smoothed to result in bars having dimensions of 25*2.5*2.0 mm which were then polished using SiC-paper of grain size 1000. The edges were also beveled with SiC-paper of grain size 1000. The span was 20 mm. The results are comparable to biaxial strength results.

In addition to this, fracture toughness was determined by applying a Vickers indentation onto a polished surface and measuring the size of the flaws originating from the edges (Indentation Force Method . . . IF). This method is useful as comparative method but does not result in absolute values. For comparison measurements were performed on notched bending samples (SENB, SEVNB). For the lithium disilicate glass ceramics fracture toughness values >2 MPam$^{0.5}$ were obtained.

In Table II the values for the biaxial strength and the fracture toughness of the samples having the disilicate phase, i.e. those samples that were crystallized twice, are given. In addition to that quotients are given which give the ratio of the biaxial strength of the disilicate system to the biaxial strength of the metasilicate system (biaxial solidification factor or Strength Increase Factor) or the ratio of the fracture toughness of the disilicate system to the fracture toughness of the metasilicate system (solidification factor $K_{IC}$ or Fracture Toughness Increase Factor).

Translucence was determined after the second crystallization: a test piece 16 mm diameter and having a thickness of 2 mm was prepared and polished on both sides. The contrast value CR was determined according to BS 5612 (British Standard) using a spectral colorimeter (Minolta CM-3700d). The determination of the contrast value consisted of two single measurements. The test piece to be analyzed is therefor placed in front of a black ceramic body having a reflexion of 4% at most and accordingly in front of a white ceramic body having a reflexion of 86% at minimum which are then colourmetrically determined. Using highly transparent test pieces reflexion/absorption is mainly caused by the ceramic background whereas reflexion is caused by the test piece in case an opaque material is used. The ratio of reflected light on black ground to reflected light on white ground is the quantum for the contrast value, with total translucence leading to a contrast value of 0 and total opaquescence leading to a contrast value of 1. The samples were rated as follows:

extraordinary: CR<0.4
very good: 0.4<CR<0.5
good: 0.5<CR<0.6
acceptable: 0.6<CR<0.8
opaque: 0.8<CR.

TABLE III

| Expl No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| KBT [° C.] | 500 | 490 | 520 | 500 | 500 | 500 | 500 | 500 | 500 | 500 | 520 | 500 | 500 | 500 | 500 | 500 | 500 | 500 | 500 | 500 |
| KBt [min] | 10 | 30 | 5 | 30 | 10 | 10 | 10 | 10 | 10 | 10 | 10 | 10 | 7 | 7 | 7 | 10 | 20 | 10 | 10 | 30 |
| wt % | | | | | | | | | | | | | | | | | | | | — |
| $SiO_2$ | 69.3 | 73.0 | 64.0 | 68.1 | 70.1 | 69.0 | 68.6 | 69.9 | 68.6 | 68.8 | 70.0 | 65.7 | 67.4 | 68.4 | 65.0 | 70.0 | 70.0 | 67.8 | 68.3 | 67.7 |
| $K_2O$ | 4.3 | 4.4 | 4.2 | 4.2 | 4.5 | 4.3 | 4.3 | 4.4 | 2.0 | 5.0 | 5.0 | 4.1 | 4.0 | 2.7 | 2.0 | 4.4 | 3.8 | 4.1 | 4.3 | 4.2 |
| $Na_2O$ | | | | | | | | | 2.0 | | | | 0.1 | 1.0 | | 0.1 | 0.1 | 0.1 | | |
| SrO | | | | | | 2.0 | | | | | | | | | 2.0 | | | | | |
| BaO | | | 2.0 | | | | 2.0 | | | | | | | | 2.0 | | | | | |
| CaO | | | | | | | | 2.0 | | | | | | | 1.0 | | | | | |
| $Li_2O$ | 15.3 | 17.0 | 13.0 | 15.0 | 15.5 | 15.2 | 15.1 | 15.4 | 15.1 | 15.1 | 15.0 | 14.5 | 14.8 | 15.0 | 14.0 | 16.0 | 16.0 | 15.0 | 15.1 | 14.9 |
| $Al_2O_3$ | 1.1 | 1.1 | 4.0 | 5.0 | 1.1 | 1.1 | 1.1 | 1.1 | 3.0 | 1.1 | 1.1 | 1.1 | 1.1 | 3.0 | 4.1 | 1.8 | 1.1 | 1.1 | 0.0 | 0.0 |
| $P_2O_5$ | 3.8 | 3.8 | 3.8 | 3.8 | 3.8 | 3.8 | 3.8 | 3.8 | 5.0 | 3.8 | 2.0 | 3.8 | 3.8 | 3.5 | 3.8 | 3.8 | 3.8 | 3.8 | 3.8 | 3.8 |
| MgO | 1.0 | 0.0 | 1.0 | 0.0 | 5.0 | 1.0 | 1.0 | 1.0 | 0.0 | 1.0 | 0.9 | 1.0 | 0.5 | 0.1 | 0.0 | 0.3 | 0.1 | 0.1 | 1.0 | 1.0 |
| $ZrO_2$ | | | | | | | | | | 2.o | | 1.0 | 0.1 | 0.1 | 0.1 | 0.1 | 0.1 | 0.1 | | |
| ZnO | 5.2 | 0.7 | 6.0 | 3.9 | 0.0 | 3.6 | 4.1 | 2.4 | 4.3 | 3.2 | 6.0 | 2.8 | 4.7 | 5.2 | 4.0 | 2.0 | 4.5 | 4.8 | 5.1 | 5.0 |
| $TiO_2$ | | | | | | | | | | | | | | | | | | | | 1.6 |
| $V_2O_5$ | | | | | | | | | | | | | 0.2 | | | | | | | |
| $Fe_2O_3$ | | | | | | | | | | | | | | | | | | | | 0.2 |
| $MnO_2$ | | | | | | | | | | | | | 0.2 | | | | | | | 0.5 |
| $CeO_2$ | | | 2.0 | | | | | | | | | 0.5 | 2.0 | 1.0 | 0.4 | 1.0 | 0.4 | 0.5 | | |
| $Y_2O_3$ | | | | | | | | | | | | | | | | | | | 2.4 | |
| $La_2O_3$ | | | | | | | | | | | | 0.5 | 0.3 | | 1.0 | 0.1 | 0.1 | 0.3 | | 3.4 |
| $Pr_2O_3$ | | | | | | | | | | | | 1.0 | | | | | | | | |
| $Ta_2O_5$ | | | | | | | | | | | | 1.5 | | | | | | | | |
| $Tb_4O_7$ | | | | | | | | | | | | 1.5 | 0.5 | | 0.5 | 0.5 | | | | |
| $Er_2O_3$ | | | | | | | | | | | | 1.0 | 0.3 | | | | | | | |
| | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |

TABLE IV

| Ex. No. | 1 | 2 | 3 | 4 | 5 | 6 | 7 | 8 | 9 | 10 |
|---|---|---|---|---|---|---|---|---|---|---|
| phases present after 1st crystallisation | LS | LS, LS2 | LS | LS | LS, LS2 | LS | LS | LS, LS2 | LS | LS |
| phases present after 2nd crystallisation | LS2, LP | LS2, LP | LS2, LP | LS2, LP | LS2, LP | 1S2, LP | LS2, LP | LS2, LP | LS2, LP | LS2, LP |

TABLE IV-continued

| | | | | | | | | | | |
|---|---|---|---|---|---|---|---|---|---|---|
| biaxial strength after 2nd crystallisation | 359 | 424 | 250 | 314 | 324 | 472 | 426 | 404 | 356 | 319 |
| biaxial solidification factor (Strength Increase Factor) | 3.0 | 2.4 | 2.5 | 3.4 | 2.4 | 3.5 | 3.5 | 2.3 | 3.2 | 2.7 |
| K1C [MPm$^{0.5}$] after 2nd crystallisation | 1.6 | 2.2 | 1.9 | 1.9 | 1.8 | 2.3 | 1.8 | 2.4 | 1.9 | 1.8 |
| K1C solidification factor ($K_{1C}$ Increase Factor) | 1.8 | 1.7 | 2.6 | 2.5 | 1.6 | 2.4 | 2.0 | 1.9 | 1.9 | 1.8 |
| grinding time in comparison to ProCAD | 93% | 103% | 95% | 89% | 98% | 93% | 94% | 105% | 94% | 94% |
| Machinability | very good | good | very good | very good | good | very good | very good | good | very good | very good |
| edge strength | Good | very good | good | good | good | good | acceptable | good | acceptable | good |
| Translucency | very good | n.m. | n.m. | n.m. | n.m. | extraordinary | n.m | n.m. | acceptable | n.m. |
| chemical durability (ISO 6872) | Good | good | good | good | good | good | good | good | good | good |

| Ex. No. | 11 | 12 | 13 | 14 | 15 | 16 | 17 | 18 | 19 | 20 |
|---|---|---|---|---|---|---|---|---|---|---|
| phases present after 1st crystallisation | LS, LS2 | LS | LS | LS | LS | LS | LS | LS | LS2 | LS2 |
| phases present after 2nd crystallisation | LS2, LP | LS2, LP | LS2, LP | LS2, LP | LS2, LP | LS2, LP | LS2, LP | LS2, LP | LS2, LP | LS2, LP |
| biaxial strength after 2nd crystallisation | 301 | 354 | 381 | 389 | 342 | 329 | 420 | 387 | 440 | 405 |
| biaxial solidification factor (Strength Increase Factor) | 1.7 | 2.9 | 3.0 | 3.1 | 2.6 | 2.9 | 3.2 | 3.4 | 2.2 | 2.1 |
| K1C [MPm$^{0.5}$] after 2nd crystallization | 2.1 | 2.0 | 1.9 | 2.0 | 1.8 | 1.7 | 2.1 | 1.9 | 1.8 | 1.9 |
| K1C solidification factor ($K_{1C}$ Increase Factor) | 1.6 | 1.9 | 2.1 | 1.8 | 2.0 | 1.6 | 2.2 | 1.9 | 1.0 | 1.5 |
| grinding time in comparison to ProCAD | 115% | 98% | 90% | 91% | 94% | 100% | 95% | 94% | 119% | 129% |
| Machinability | Acceptable | very good | very good | very good | very good | good | good | very good | poor | poor |
| edge strength | Good | acceptable | very good | very good | very good | very good | very good | good | good | good |
| translucency | n.m. | n.m. | n.m. | n.m. | n.m. | n.m. | n.m. | n.m. | n.m. | n.m. |
| chemical durability (ISO 6872) | Good | good | good | good | good | good | good | good | good | good |

The data in Table II show that the lithium metasilicate glass ceramics combine a very good machinability and high edge strength with the easy possibility to convert them by a simple heat treatment into lithium disilicate glass ceramics which have a very high bending strength as well as an excellent chemical durability and good translucence, all of which being properties which make them very attractive as materials useful for the manufacture of dental restorations.

In the following some examples are described in more detail:

Example 1

The glass was molten at a temperature of 1500° C. for 3 hours and was then poured into steel moulds which were preheated to 300° C. After one minute the glass bars were transferred into a cooling furnace and were tempered at 500° C. for 10 minutes and then cooled to room temperature.

The glass was homogeneous and transparent.

Following the glass bar was subjected to a first crystallization at 650° C. for a period of 20 minutes.

From the such ceramized bar, discs were sawn out of a round bar, and biaxial strength was measured. The phase content was analyzed via XRD (X-ray diffraction). Lithium metasilicate was the only phase that was detected. Biaxial strength was 119+/−25 MPa.

Also the milling time of test bodys was measured. The milling time of the test body was one minute below that of ProCAD®, which was used as reference.

The edge strength was good.

Additional 10 discs were subjected to a second crystallization at 850° C. for a period of 10 minutes and biaxial strength and fracture toughness were measured.

Biaxial strength was 359+/−117 MPa which correlates to a Strength Increase Factor of 3.0.

Fracture toughness (IF) was 1.6 MPam$^{0.5}$.

Translucence was very good.

The chemical stability according to ISO 6872 (4% acetic acid, 80° C., 16 h) was 37 pg/cm$^2$.

Example 6

Glass bars were produced according to example 1. The glass again was homogeneous and transparent.

The first crystallization was performed at 650° C. for a period of 20 minutes.

Lithium metasilicate was determined to be the main phase with traces of lithium disilicate also being present. Biaxial strength was 135+/−24 MPa.

Again the milling time of a test body was measured. The milling time of the test body was one minute below that of ProCAD®, which again was used as reference.

The edge strength was very good.

After a second crystallization which was performed according to example 1 the biaxial strength was 472+/−85 MPa which correlates to a Strength Increase Factor of 3.5.

Fracture toughness (IF) was 2.3 MPam$^{0.5}$.

Translucence was extraordinary.

Example 9

Glass bars were produced according to example 1. The glass again was homogeneous and transparent.

The first crystallization was performed at 650° C. for a period of 20 minutes.

Lithium metasilicate was determined to be the only phase. Biaxial strength was 112+/−13 MPa.

Again the milling time of a test body was measured. The milling time of the test body was one minute below that of ProCAD®, which again was used as reference.

The edge strength was good.

After a second crystallization which was performed according to example 1 the biaxial strength was 356+/−96 MPa which correlates to a Strength Increase Factor of 3.16.

Fracture toughness (I F) was 1.9 MPam$^{0.5}$.

Translucence was acceptable.

Example 20 (Comparison)

Glass bars were produced according to example 1. The glass again was homogeneous and transparent.

The first crystallization was performed at 650° C. for a period of 20 minutes.

Lithium disilicate was determined as the main phase and lithium metasilicate was only present in traces. Biaxial strength was 194+/−35 MPa.

Again the milling time of a test body was measured. The milling time of the test body was four minutes longer that of ProCAD®, which again was used as reference.

The edge strength was poor.

After a second crystallization which was performed according to example 1 the biaxial strength was 405+/−80 MPa which correlates to a Strength Increase Factor of 2.09.

Fracture toughness (IF) was 1.88 MPam$^{0.5}$.

Translucence was very good.

This example makes it even more obvious that in the light of the glass ceramic materials according to the invention the adverse properties in respect to machinability of the prior art material disqualify same to be used in applications as are mentioned above.

The following examples 21 to 23 show the usefulness of the lithium silicate glass according to the invention which comprises nuclei suitable for the formation of lithium metasilicate and subsequently lithium disilicate glass ceramics.

Example 21

A glass melt having the composition according to example 14 was melted in a platinum crucible at a temperature of 1500° C. for 3 hours. The glass was not poured in a steel mould, but quenched in water.

Thus, a glass granulate formed which was dried and subsequently heated to 500° C. for 30 minutes to produce nuclei suitable for the formation of lithium metasilicate crystals. The obtained glass was milled to a particle size of less than 45 pm.

The obtained powder was mixed with a modeling liquid consisting of more than 95% water and additives for improving moldability and layered on a crown cap of densely sintered zirconium oxide, e.g. DCS-zircon.

The crown cap was fired in a dental furnace at a temperature of 900° C. with 2 minutes holding time. By this procedure the applied glass powder containing nuclei for the crystallization was simultaneously crystallized and densely sintered so that a dentine core of lithium disilicate glass ceramic resulted. On this core a suitable incisal mass having a suitable expansion coefficient was applied.

The final anterior tooth restoration showed good resistance against rapid temperature changes up to 160° C. This proves a good bond between the dentine layer of lithium disilicate glass ceramic and the framework of high-strength zirconium oxide.

Example 22

Bars of a glass having a composition according to example 14 were prepared in the same manner as in example 1. The glass bars were homogenous, transparent and light yellow coloured. A crown cap of densely-sintered zirconium oxide was circularly reduced. Subsequently a dentine core was layered with dental wax and the crown margin was modeled on the stump. The restoration was provided with a cast-on channel. The crown cap was applied on a muffle basis and embedded in investment material, (Empress Speed, Ivoclar). After the required binding time the muffle was preheated to 850° C. resulting in the removal of the wax. After 90 minutes a blank of the above lithium silicate glass having nuclei for forming lithium metasilicate was put in the muffle and pressed on the cap of zirconium oxide in accordance with the known Empress-hot pressing process at 900° C. This resulted in crystallization of the glass blank to a lithium disilicate glass ceramic.

After divesting, the final product was a zirconium oxide cap having a dentine layer of lithium disilicate glass ceramic. This dental restoration showed an excellent fit of the circular edge on the model. Furthermore, the so-prepared dentine layer was free from porosities.

Example 23

A metal cap of an alloy having an expansion coefficient of 12.8*10$^{-6}$ 1/K and a solidification temperature of 11000° C. was prepared in a cast process, sand-blasted and by an oxidation-firing step prepared for the further processing.

In an analogous manner as in example 22 a dentine core was applied on the cap using modeling wax. The metal cap was embedded, and the wax was removed by firing in a furnace. As in example 22 a blank of the lithium silicate glass having suitable nuclei was hot-pressed on the metal cap at 900° C.

The so-prepared dental restoration showed a good bond between metal framework and the lithium disilicate glass ceramic and also had a high resistance against drastic temperature changes of above 160° C.

It is a further embodiment of the present invention to provide methods of mass-production of strong and aesthetic dental restorations using lithium silicate blanks and at least 4-axis or higher order (more axes) CNC machines. More specifically, this embodiment is related to milling strategies especially useful for machining lithium silicate blanks using 5-axis or higher order computer numerical controlled (CNC) machines equipped with robotic and automated loading features. The CNC machine can include a computer (CPU), CNC control unit, memory device and/or software package.

Prior examples describe machining lithium silicate blanks of this invention using CEREC (Sirona, Germany) and DCS Precimill (DCS, Switzerland) CAD/CAM systems. While Sirona CEREC inLab is representative of a compact, benchtop, dental CAD/CAM system capable of milling a variety of machinable ceramics and other reasonably weak and soft materials, DCS Precimill is a much larger and stiffer machine than CEREC. The DCS Precimill machine can mill much stronger and harder materials such as titanium alloys and fully dense zirconia. Both machines have been specifically developed as dental CAD/CAM systems for the dental laboratory environment, each utilizing its own, unique milling strategy and tool paths which suffer from a number of disadvantages if used for machining lithium disilicate blanks.

It is important to recognize that total per unit fabrication time for a given CAD/CAM system consists of at least milling time and set-up time (i.e., set up of the machine and the software configuration for each new case that can include installing a new block and loading a new case/file). CEREC inLab is a very efficient system for milling one block at a time as it utilizes two grinding tools (diamond burs) simultaneously. The outside surface is machined with a round-tip cylindrical diamond bur at the same time as the inside surface of the dental restoration is machined with a stepped-cylindrical or conical (tapered) diamond bur. As a result, it takes about 25 minutes to mill a standard full-contour molar (which may be defined as an average size full contour molar crown of generic design such as tooth #30 on Ivoclar Vivadent Model #594148) or even less, about 20 minutes, on a new CEREC MC XL machine. Nevertheless, manual blank installation and software preparation steps take at least a few minutes noticeably increasing total per-unit fabrication time to about 25-30 minutes. It is also important to note that the Sirona system utilizes fairly small diamond burs with a grit or grain size of less than 60 microns. The resulting biaxial strength exceeds 300 MPa. The DCS system is a larger machine lacking optimal milling strategies and tool paths for lithium silicate blanks and also is not equipped with robotic/automated loading features, therefore yielding unfavorably large per-unit time if used for milling lithium silicate restorations. As a result, both machines are not optimal for milling centers and central processing facility environments requiring shorter fabrication times per unit and system capacity for automation.

Grinding tools may include a diamond coating comprising single crystal or polycrystalline diamonds of a certain grain (grit) size. Grinding tools may include a diamond coating of a certain grit size. The power of the grinding tools (i.e., the material removal rate for a given applied force and depth of cut) is proportional to the diamond coating grain size minus the embedding depth of the diamond grains in the bonding layer. This is discussed in an article by Dmitri Wiebe, Isabella Maria Zylla. "Assessment of the Grinding Power and Service Life of Galvanically Diamond Coated Grinding Tools". Journal of Applied Research, Vol. 7, No. 1, March 2007, pp 138-145.), which is hereby incorporated by reference. Depth of cut, sometimes referred to as lateral lining, is the distance that a tool penetrates into the work piece on each pass and it often depends on the diamond grain size distribution on the tool, which is sometimes characterized by diamond grit size in microns. Coarser, more even-sized embedded diamond grit, more uniformly distributed in the coating may also allow increasing depth of cut and easier removal of debris.

Coarser diamond grit size of the grinding/milling tool allows for an increase in the feed rate and the depth of cut, which results in a higher material removal rate and a lower milling time. Unfortunately, it also increases surface damage, i.e. the size of surface flaws, which results in lower strength. Therefore, a compromise is required between milling time and the minimally acceptable target strength of the material based on its clinical indications, i.e., ≥300 MPa for lithium disilicate restorations (fixed prostheses) fabricated by heat treating of milled lithium silicate dental articles, which belong to Type II Classes 3 and 4 dental ceramics according to ISO6872:2008. This dilemma severely limits the productivity of milling centers utilizing existing dental CAD/CAM systems using prior art milling strategies and tool paths.

Embodiments of the present invention teach milling strategies that allow the use of coarse diamond milling tools without having to compromise the final strength of the milled lithium silicate material, thus allowing for a reduction in milling time. In order to determine the allowable size of the diamond grit that may be used for milling dental ceramic blanks, the size of allowable surface and volume critical flaws of the material to be machined must be determined.

One example of a preferred material for milling dental articles using the strategies herein is lithium silicate. The final flexural strength and fracture toughness and the respective strength and toughness factors set forth in Table IV were used to calculate the strength and fracture toughness of the lithium silicate materials in Examples 1 through 20 after the $1^{st}$ crystallization (also referred to as the "machinable condition" of the lithium silicate materials for milling or machining, prior to subsequent heat treatment or crystallization steps). Table V presents the calculated flexural strength and fracture toughness of lithium silicate materials from Examples 1 through 20 in "machinable condition" corresponding to data provided in Table IV on final strength and fracture toughness (after $2^{nd}$ crystallization), and strength/fracture toughness increase factors.

TABLE V

| Example Number | Flexural Strength ($\sigma_f$), MPa | | | | Fracture Toughness ($K_{Ic}$), MPa·m$^{1/2}$ | | | Edge Strength |
|---|---|---|---|---|---|---|---|---|
| | Final | Machinable Condition | SIF* | Machinability | Final | Machinable Condition | TIF** | |
| 1 | 359 | 120 | 3.0 | very good | 1.6 | 0.9 | 1.8 | good |
| 2 | 424 | 177 | 2.4 | good | 2.2 | 1.3 | 1.7 | very good |
| 3 | 250 | 100 | 2.5 | very good | 1.9 | 0.7 | 2.6 | good |

TABLE V-continued

| Example Number | Flexural Strength ($\sigma_f$), MPa | | | | Fracture Toughness ($K_{Ic}$), MPa · m$^{1/2}$ | | | Edge Strength |
|---|---|---|---|---|---|---|---|---|
| | Final | Machinable Condition | SIF* | Machinability | Final | Machinable Condition | TIF** | |
| 4 | 314 | 92 | 3.4 | very good | 1.9 | 0.8 | 2.5 | good |
| 5 | 324 | 135 | 2.4 | good | 1.8 | 1.1 | 1.6 | good |
| 6 | 472 | 135 | 3.5 | very good | 2.3 | 1.0 | 2.4 | good |
| 7 | 426 | 122 | 3.5 | very good | 1.8 | 0.9 | 2.0 | acceptable |
| 8 | 404 | 176 | 2.3 | good | 2.4 | 1.3 | 1.9 | good |
| 9 | 356 | 111 | 3.2 | very good | 1.9 | 1.0 | 1.9 | acceptable |
| 10 | 319 | 118 | 2.7 | very good | 1.8 | 1.0 | 1.8 | good |
| 11 | 301 | 177 | 1.7 | acceptable | 2.1 | 1.3 | 1.6 | good |
| 12 | 354 | 122 | 2.9 | very good | 2 | 1.1 | 1.9 | acceptable |
| 13 | 381 | 127 | 3.0 | very good | 1.9 | 0.9 | 2.1 | very good |
| 14 | 389 | 125 | 3.1 | very good | 2 | 1.1 | 1.8 | very good |
| 15 | 342 | 132 | 2.6 | very good | 1.8 | 0.9 | 2.0 | very good |
| 16 | 329 | 113 | 2.9 | good | 1.7 | 1.1 | 1.6 | very good |
| 17 | 420 | 131 | 3.2 | good | 2.1 | 1.0 | 2.2 | very good |
| 18 | 387 | 114 | 3.4 | very good | 1.9 | 1.0 | 1.9 | good |
| 19 | 440 | 200 | 2.2 | poor | 1.8 | 1.8 | 1.0 | good |
| 20 | 405 | 193 | 2.1 | poor | 1.9 | 1.3 | 1.5 | good |

*Strength Increase Factor;
**Fracture Toughness Increase Factor

The flexural strength and fracture toughness of the lithium silicate materials in machinable condition (i.e., prior to the second crystallization step) were then used to calculate the surface and volume critical flaw sizes using the Griffith-Irwin equation (Equation 1 below)

$$K_{Ic} = Y\sigma_f C^{1/2} \quad \{\text{Eq. 1}\}$$

or $$C = (K_{Ic}/Y\sigma_f)^2 \quad \{\text{Eq. 2}\}$$

or $$\sigma_f = K_{Ic}/(Yc^{1/2}) \quad \{\text{Eq. 3}\}$$

where C is the length of the critical flaw size for surface cracks (surface failure origin)
2C is the length of the critical flaw size for volume cracks (volume failure origin)
$K_{Ic}$ is the fracture toughness or critical stress intensity factor
$\sigma_f$ is the stress at fracture or flexural strength
Y is a geometrical factor or constant that depends on the type of critical flaw, i.e., location, orientation and geometry of the critical flaw and loading configuration; Y is assumed to be roughly equal to 1 for pure Mode I fracture (plain strain loading configuration), 1.24 (semicircular) or 1.94 (shallow cracks), wherein Y=1 is the maximum critical flaw size.

The Griffith-Irwin equation is discussed in an article by Alvaro Della Bona, John J. Mecholsky Jr., Kenneth J. Anusavice entitled "Fracture behavior of lithia disilicate- and leucite-based ceramics" in Dental Materials (2004) 20, pp 956-962, which is hereby incorporated by reference. Geometrical factors given in the aforementioned article by Della Bona et al., allow using flexural strength values to calculate critical flaw sizes for different crack configurations based on known fracture toughness values. According to Equation 3 above, the larger the geometric factor (Y) the more dangerous, more strength limiting this particular flaw/loading configuration is, resulting in lower final flexural strength values or even failure of the part during milling.

Table VI sets forth surface and volume critical flaw sizes calculated using the equation above (Equation 1) from flexural strength and fracture toughness values of Table V and geometrical factor values (Y).

TABLE VI

| Properties of lithium silicate blanks in machinable condition Example No. | | | Critical Surface Flaw Size, microns | | | Critical Volume Flaw Size, microns | | |
|---|---|---|---|---|---|---|---|---|
| | | | Crack Type/Configuration | | | | | |
| | $\sigma_f$, MPa | $K_{Ic}$, MPa · m$^{1/2}$ | shallow cracks Y = 1.94 | semi-circular Y = 1.24 | plain strain Y = 1 | shallow cracks Y = 1.94 | circular Y = 1.24 | plain strain Y = 1 |
| 1 | 120 | 0.9 | 15 | 36 | 55 | 29 | 72 | 110 |
| 2 | 177 | 1.3 | 14 | 35 | 54 | 29 | 70 | 107 |
| 3 | 100 | 0.7 | 14 | 35 | 53 | 28 | 69 | 107 |
| 4 | 92 | 0.8 | 18 | 44 | 68 | 36 | 88 | 135 |
| 5 | 135 | 1.1 | 18 | 45 | 69 | 37 | 90 | 139 |
| 6 | 135 | 1.0 | 13 | 33 | 50 | 27 | 66 | 101 |
| 7 | 122 | 0.9 | 15 | 36 | 55 | 29 | 71 | 109 |
| 8 | 176 | 1.3 | 14 | 34 | 52 | 27 | 67 | 103 |
| 9 | 111 | 1.0 | 21 | 53 | 81 | 43 | 105 | 162 |
| 10 | 118 | 1.0 | 19 | 47 | 72 | 38 | 93 | 143 |
| 11 | 177 | 1.3 | 15 | 36 | 55 | 29 | 71 | 110 |
| 12 | 122 | 1.1 | 20 | 48 | 74 | 40 | 97 | 149 |
| 13 | 127 | 0.9 | 13 | 33 | 51 | 27 | 66 | 102 |
| 14 | 125 | 1.1 | 21 | 51 | 78 | 42 | 102 | 157 |
| 15 | 132 | 0.9 | 12 | 30 | 47 | 25 | 61 | 94 |
| 16 | 113 | 1.1 | 23 | 57 | 88 | 47 | 114 | 175 |
| 17 | 131 | 1.0 | 14 | 34 | 53 | 28 | 69 | 106 |
| 18 | 114 | 1.0 | 21 | 50 | 77 | 41 | 100 | 154 |
| 19 | 200 | 1.8 | 22 | 53 | 81 | 43 | 105 | 162 |
| 20 | 193 | 1.3 | 11 | 28 | 43 | 23 | 23 | 86 |

Figure 8:
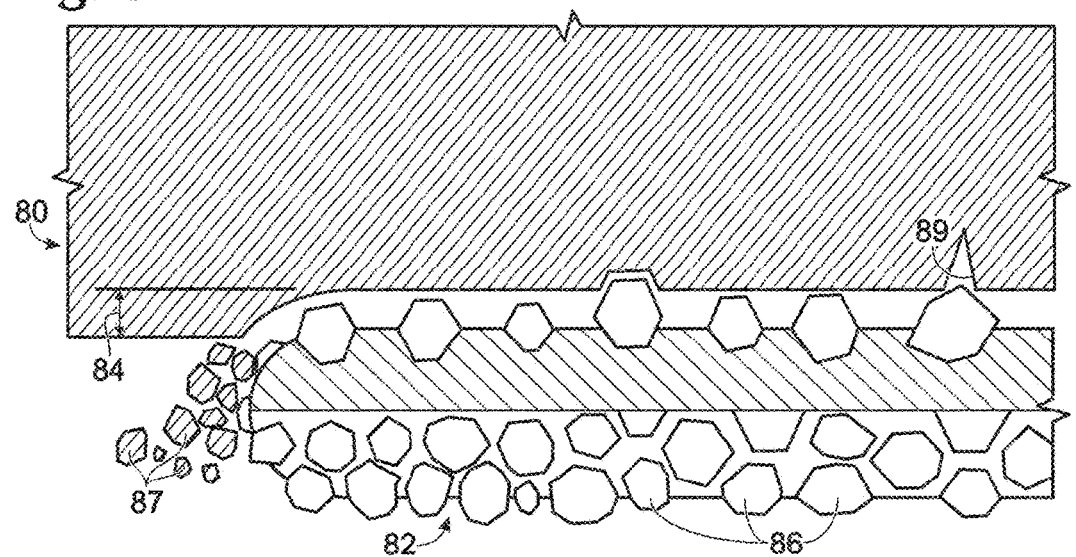
FIG. 8 shows a schematic diagram of a block of material during an embodiment of a milling operation of the present invention.

Reference is made to FIG. 8, which shows a block of material 80 undergoing a milling process with a diamond grinding tool 82. Diamond tool 82 has a plurality of diamond grains 86 embedded in tool 82. FIG. 8 illustrates the relation of the diamond grain size or diamond grit and the embedding depth of the diamond grains in the bonding layer to the optimum depth of cut and scratch/surface flaw size. Block 80 is milled layer by layer, the depth of cut 84, also known as lateral lining, is the thickness of the layer being removed and/or the distance the tool penetrates the block on each pass of debris 87 being removed from block 80. Although there is no limitation on the thickness of the layer being removed, it is preferable that the thickness of the layer being removed on each pass (lateral lining) or depth of cut be less than the diamond grain size (grit size) in the range of approximately 10 to approximately 130 microns, and preferably in the range of approximately 20 to approximately 100 microns. A flaw 89 is shown in block 80. The flaws or scratches on block 80 resulting from milling with tool 82 may correlate with the distribution, size, shape, orientation or the variability of embedding depth of the diamond grains in the bonding layer of tool 82. It is possible that the scratches, crevices and other flaws left by grinding tool on the machined surface will scale with the diamond grit size or size of the diamond grains 86 embedded in tool 82. That is, the size of the deepest flaws that can potentially result in failure of the dental article during milling or post-fabrication (i.e. critical flaws) will be at least a fraction of the diamond grit size in microns or, in worst case scenario, can be nearly equal to the diamond grit size.

Conventional wisdom teaches that grinding power of a tapered tool is generally lower than that of cylindrical tool, as also discussed in Wiebe et al., referenced above. Conventional wisdom also teaches that diamond grit size (see FIG. 8 and discussion above) should not exceed the estimated maximal critical surface flaw size. For lithium silicate, based on the data in Table VI, that would be approximately 60 microns for lithium silicate, the average of the values set forth in Table VI for critical surface flaw size when Y=1. It appears that diamond tool selection for Sirona's CEREC machines, discussed above, was based on this conventional wisdom.

Surprisingly, it was found by the inventors herein that certain shapes of tapered diamond tools combined with certain milling strategies designed preferably for use with 5-axis or higher order milling machines would allow use of much coarser (by a factor of 1.5-2.5) diamond grit. In the milling strategies and processes herein, the size of the diamond grains (grit size) on the diamond tools may be in the range between the estimated maximal critical surface flaw size and the estimated maximal critical volume flaw size. This drastically accelerates the milling process without noticeable compromise in strength. Reference is made to Table VI wherein the estimated maximal critical surface flaw size of the lithium silicate ceramic is approximately 60 microns (column 6 of Table VI where Y=1) and the estimated maximal critical volume flaw size is approximately 130 (column 9 of Table VI where Y=1). Accordingly, the size of the diamond grit may range from approximately 40 to approximately 175 microns for the diamond grinding tools for the lithium silicate ceramic blocks, preferably in the range of approximately 60 to approximately 150 microns and most preferably in the range of approximately 90 to approximately 130 microns. The strategies described herein are in no way limited to lithium silicate materials and may be applied to all types of ceramic materials, preferably medical ceramic materials and most preferably dental ceramic materials.

Figure 9:
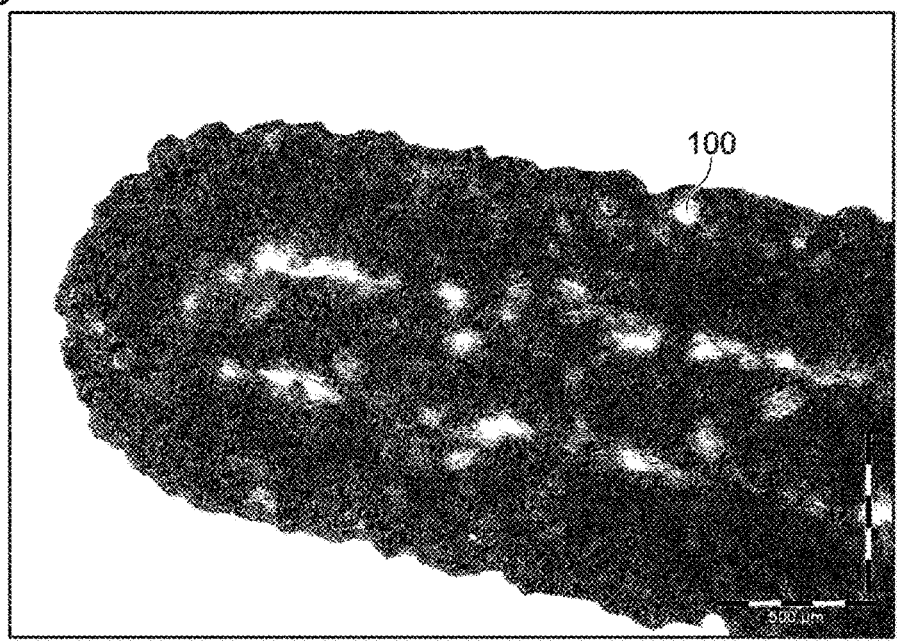
FIG. 9 shows an SEM-micrograph of a grinding tool used in an embodiment of the milling strategy of the present invention.
Figure 10:
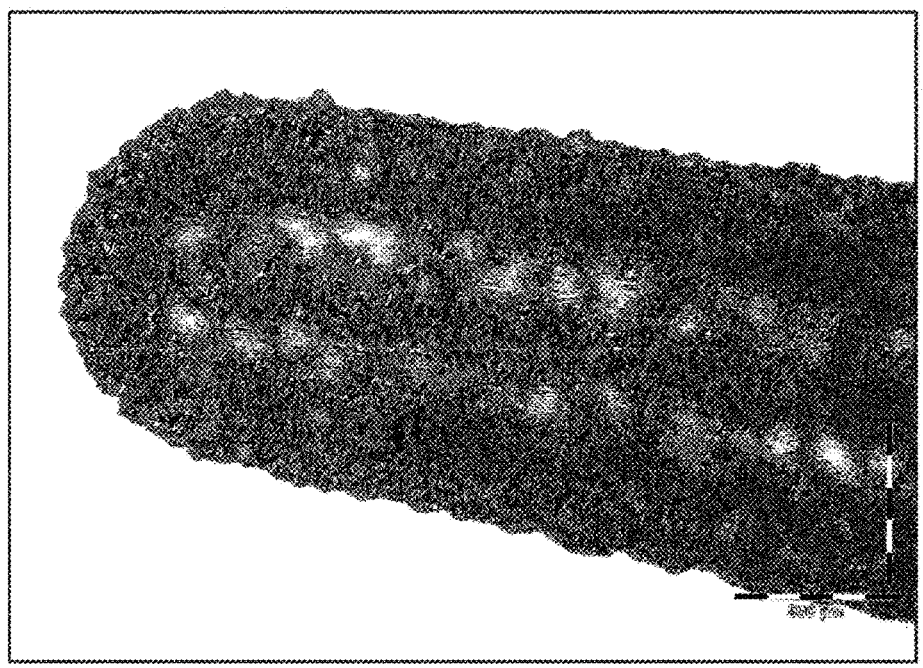
FIG. 10 shows an SEM-micrograph of a grinding tool used in an embodiment of the milling strategy of the present invention.
Figure 11:
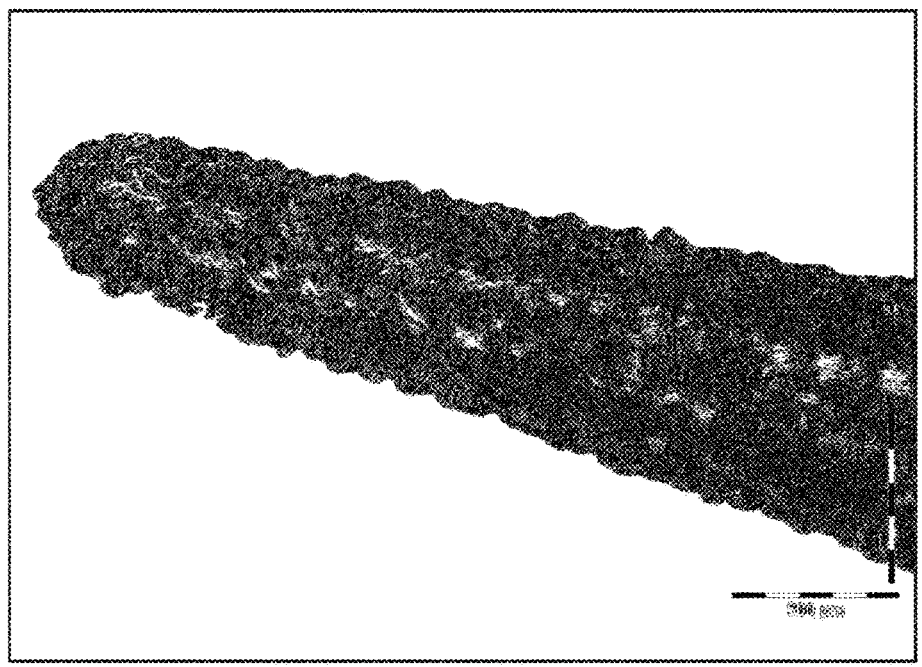
FIG. 11 shows an SEM-micrograph of a grinding tool used in an embodiment of the milling strategy of the present invention.
Figure 12:
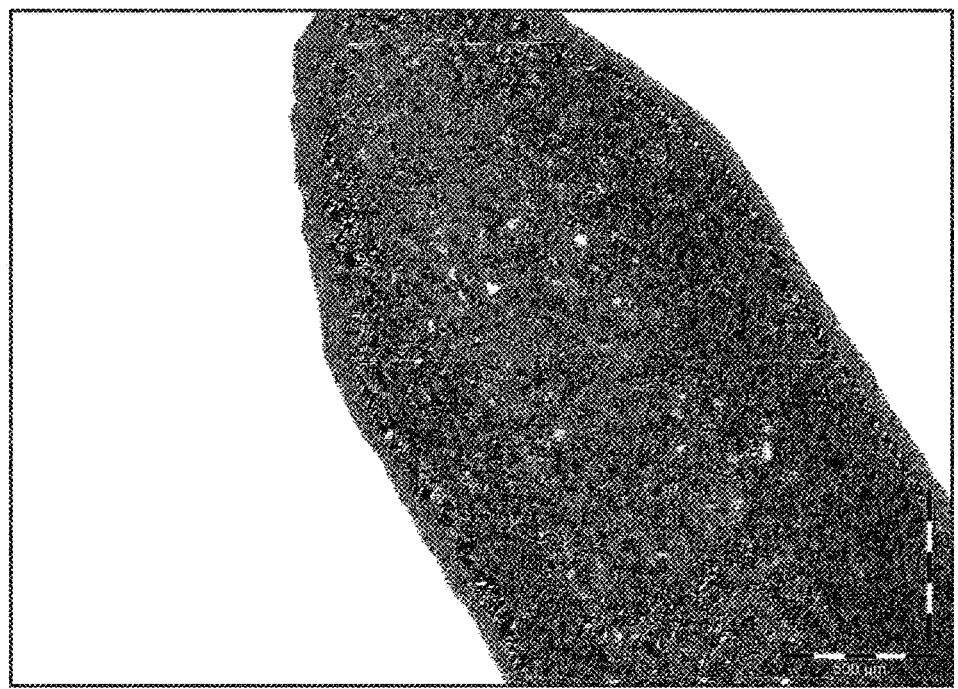
FIG. 12 shows an SEM-micrograph of a cylindrical grinding tool used in the Sirona CEREC system.
Figure 13:
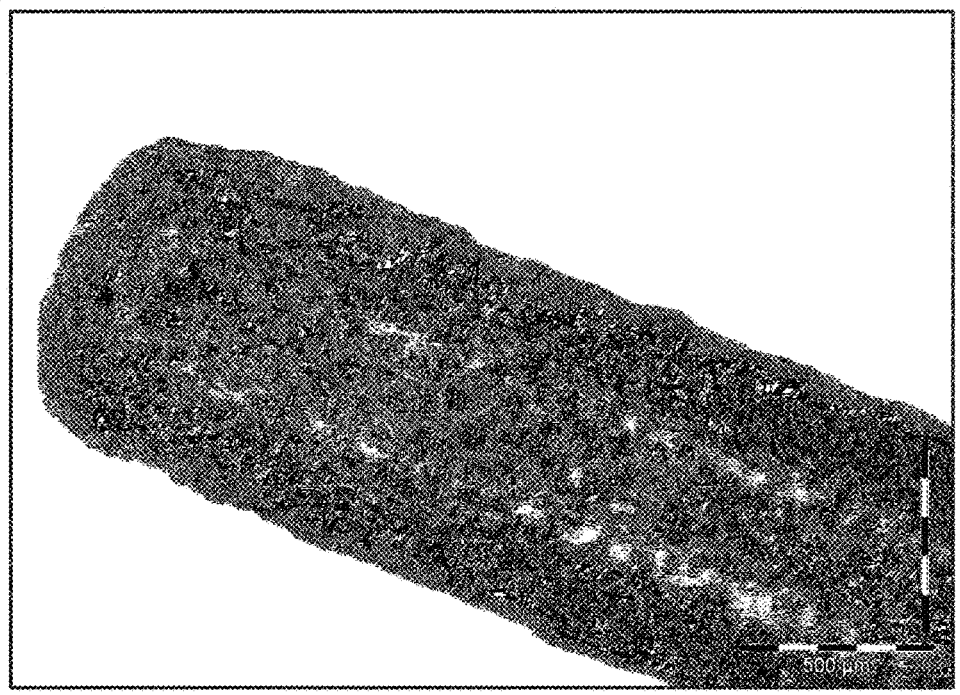
FIG. 13 shows an SEM-micrograph of a step grinding tool used in the Sirona CEREC system.

The shapes of the diamond burs are preferably conical with rounded tips (tapered round) as shown in FIGS. 9, 10 and 11. In comparison thereto, the Sirona tools used in the CEREC systems are shown in FIGS. 12 and 13. Comparing the tools used herein (FIGS. 9, 10 and 11) with those used in the Sirona CEREC system (FIGS. 12 and 13), one can see that the diamond grit of the tools used herein, is noticeably larger and substantially equiaxed. For example, in FIG. 9, a diamond grain 100 is nearly a perfect hexagon.

Figure 15C:
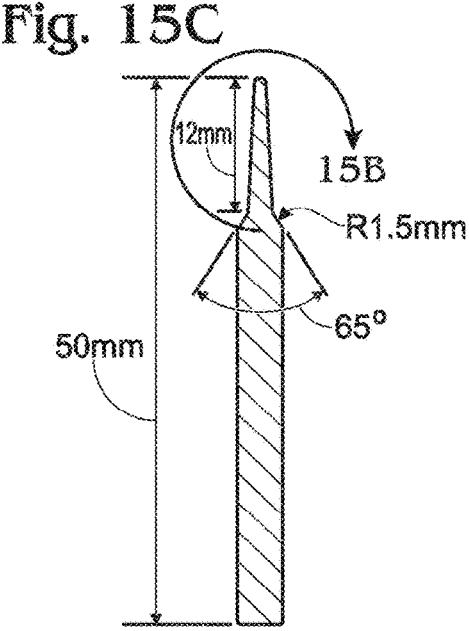
Figure 16A:
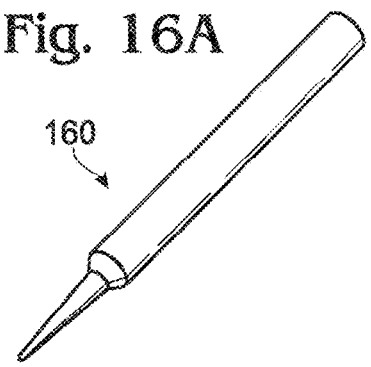
FIG. 16a shows a perspective view of the grinding tool of FIG. 11.
Figure 16B:
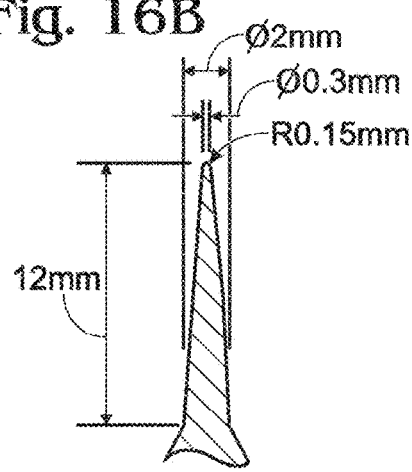
Figure 16C:
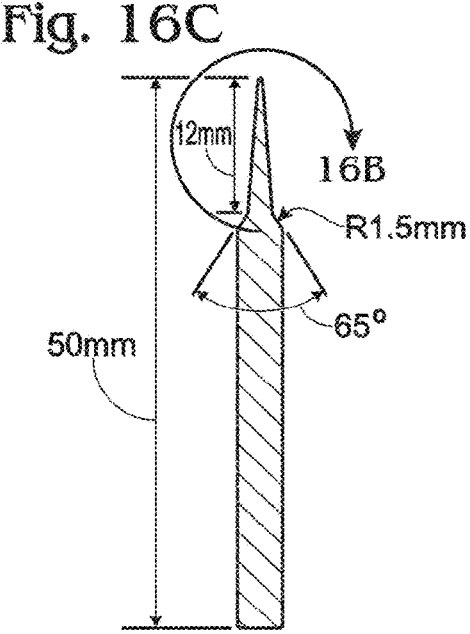
Figure 17:
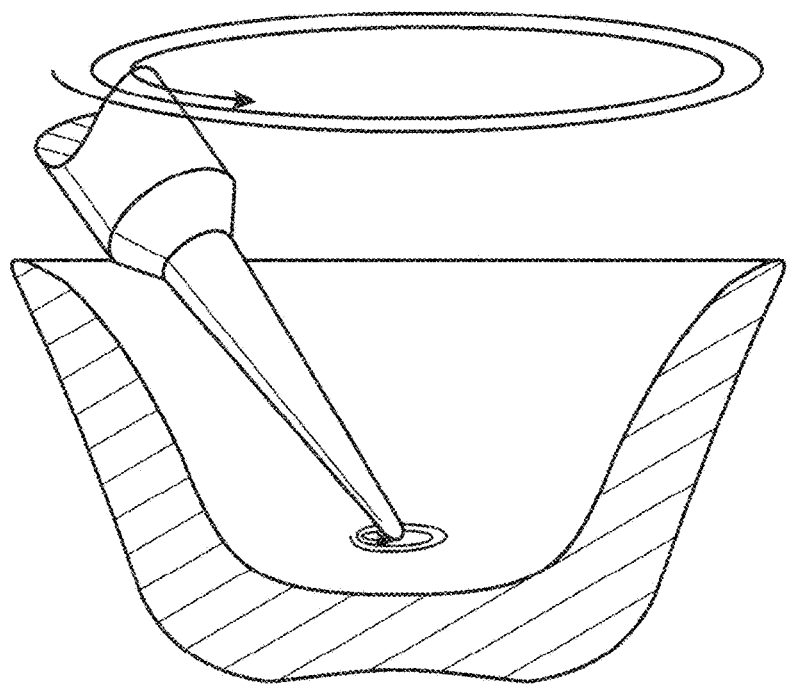
FIG. 17 shows a tool path for a machining step involving 5-axis drilling with a tapered tool.
Figure 18:
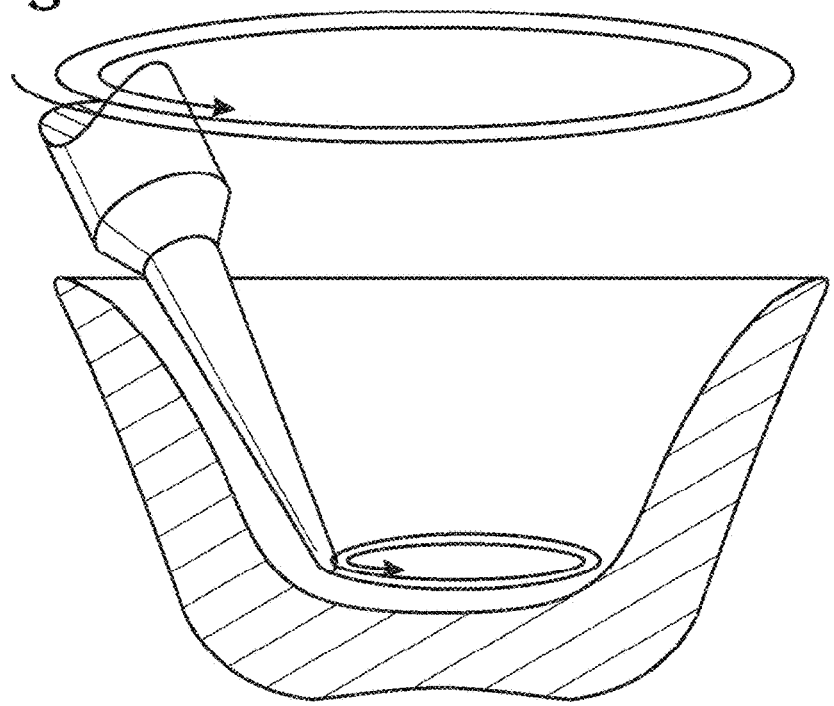
FIG. 18 shows a tool path for a machining step involving 5-axis milling with a tapered tool.

FIGS. 14a, b, and c, 15a, b, and c and 16a, b, and c show examples of specific configurations and dimensions of the tools used herein. The embodiments of the invention are not limited to the sizes and shapes shown herein. FIGS. 14a, b, and c show an example of a tool 140 that is useful for milling the interior or the inside of the article. Tool 140 has a diamond grit (grain size) of approximately 126 microns. FIGS. 15a, b, and c show a tool 150 that is useful for milling the exterior or outside of the article. Tool 150 has a diamond grit (grain size) of approximately 91 microns. FIGS. 16a, b, and c show a tool 160 that is useful for finishing the milling of the article. Tool 160 has a diamond grit of approximately 91 microns in diameter. Moreover, tool 160 also has a much finer point, the tip is approximately 0.5 mm in diameter in comparison to the tips of the tools shown in FIGS. 14 (tip is approximately 1.3 mm) and 15 (tip is approximately 1.2 mm). These tools are useful in maintaining accuracy and marginal integrity of the article during the milling process.

In addition to the tool size and diamond grit size, the milling strategies include fine, intermediate and rough machining steps. The rough, intermediate and fine milling may be dependent on a variety of factors including, but not limited to, tool specifications, revolutions per minute, linear speeds, feed rate (mm/min), feed per rotation (microns), depth of cut and material removal rate.

The milling strategies discussed herein may be combined with robotic features ("$6^{th}$ axis") of heavy duty industrial CNC machines to enable cost-effective use of such high productivity (and expensive) industrial CNC machines. These machines are equipped with robotic and automated loading features that were previously cost-prohibitive for dental use.

Specific illustration of milling strategies and milling parameters of embodiments of the present invention are presented in the nonlimiting examples below carried out using Roeders (Röders) 5-axis CNC machines (ROEDERS GmbH, Germany). Two Roeders models were used: RXP 500 DS model with 42,000 RPM and RXD5 model with 50,000 RPM. These Roeders 5-axis CNC machines are characterized by a very fast control unit capable of feed rates of up to 40,000 mm/min with a high capacity for automation. It should be mentioned that the actual feed rate of the milling process is dependent on the machine, tooling and material being milled. Normally in 5 axis milling, the CNC control unit is not able to calculate the xyz points for a constant speed. If the surface is very complex (full anatomical crown) the machine is not always capable of maintaining the defined speed. Roders has a very fast CNC control unit, but it is still not always constant in speed. The control unit and the motors make the big difference in accuracy and milling time. In addition to a computer, CNC control unit, memory device and software package, the following Table VII lists additional properties of the system.

TABLE VII

CAD/CAM SYSTEM PROPERTIES

Block processing time < 0.1 ms
Look ahead window with more than 10,000 blocks
Calculation of optimal feed rates and accelerations by taking into account the cutter path geometry and
machine dynamics in order to achieve the highest possible accuracy and shortest machining time
5 axes simultaneously
Automatic spline interpolation for outstanding dynamics; it is possible to set the tolerance values
User-defined jerk limitation ==> adjustable dynamics for high accuracy or extremely short machining times
Smoothening of the cutter path with tolerance specification for reducing the machining time by up to 35%
Automatic compensation of the rotations of the 4th and 5th axes for the cutter center or cutter tip (TCP) is
possible
Compensation of the spindle elongation in the control carried out either by a highly accurate measurement
sensor or the by the software
3D radius cutter compensation for milling programs with normal vectors

| | |
|---|---|
| Modern computer technology | Parallel computer system with PC based hardware |
| | High processor performance and large hard drive capacity |
| | CD-ROM drive is standard; other drives are available on request |
| | Standard 15" TFT monitor |
| | Standard Universal network interface |
| | Connection to the telephone network possible to enable remote diagnosis |
| Job management | Clearly structured job management for individual work pieces with corresponding programs; can also be used for multiple clamping in machines without robots |
| | If tool breakage is detected, the current job is stopped and the next job of the job list is started |
| | Interactive priority list with job and work piece parameters |
| | A robot interface for automation with various types of robot systems is available |
| | Integration of pallet identification with chips possible |
| | Interfaces to job management and planning software of work shop available |

Figure 19:
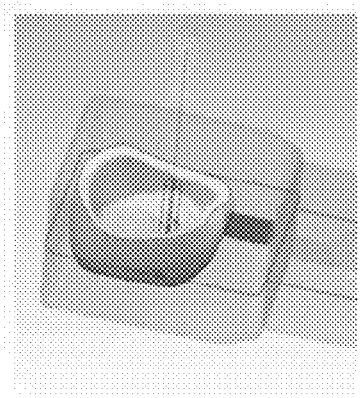
FIG. 19 shows a block with a hole pre-drilled in the block.
Figure 20:
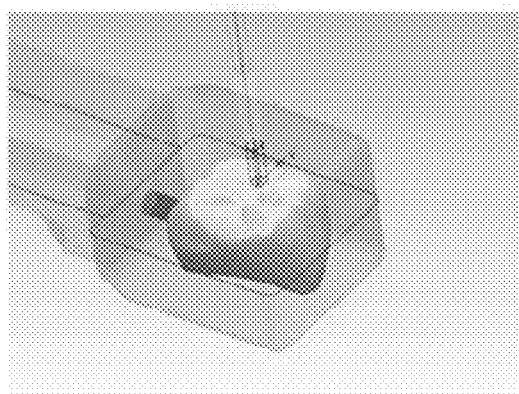
FIG. 20 shows a block with a hole pre-drilled in the block.

To further decrease the milling time necessary to fabricate a dental article, it is advantageous to provide pre-drilled holes into the blocks. This makes it easier to start the milling process. FIGS. 19 and 20 each show opposite sides of a block having holes drilled therein. In FIG. 19, the pre-drilled hole has a depth that it at least one-half the depth of the block, and more preferably at least three-fourths the depth of the block. This pre-drilled hole can be used to expedite the drilling of the underside of the dental article. In FIG. 20, the pre-drilled hole has a depth much less than one-half the depth of the block. This side can be used for the top surface of the dental article. The pre-drilled holes not only reduce milling time but also reduce wear and tear on the milling tools. FIG. 20 shows an occlusal area of a tooth drilled into block using the pre-drilled hole. FIG. 19 shows the undersurface of a tooth drilled into a block using the pre-drilled hole.

Figure 21:
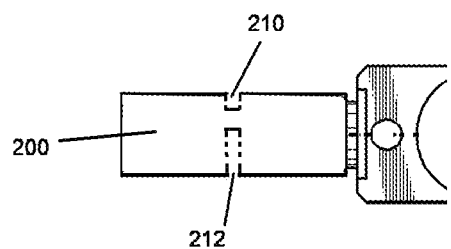
FIG. 21 shows a block with two holes predrilled in the block.

FIG. 21 illustrates the pre-drilled holes on a block 200. The upper surface of block 200 has a pre-drilled hole 210 and the lower surface of block 200 has a pre-drilled hole 212. As shown in the figure, pre-drilled holes 210 and 212 do extend entirely through to the opposing surface. Pre-drilled hole 210 provides access to block 200 for drilling the occlusal area of a tooth, as shown in FIG. 20. Pre-drilled hole 212 provides access to block 200 for drilling the undersurface of a tooth, as shown in FIG. 19.

The following examples illustrate the embodiments of the present invention directed to milling lithium silicate blanks using CNC machines integrated with dental CAD systems for automated fabrication of dental restorations known as dental CAD/CAM systems.

Examples 24 and 25

The shape to be milled was mapped onto a blank to establish the volume to be removed, which was separated into regions requiring different accuracy and surface roughness. The regions were allocated to one or more of a rough machining, intermediate machining and fine machining step. The specific tool path was calculated for each of the allocated machining steps. CAM file was generated using Dent-MILL-3-5 Axis Dental CAM software from DELCAM (Birmingham, UK). This software has some templates available for milling zirconia, titanium and non-precious alloys but not for lithium silicate or any other glass-ceramics. Therefore the custom template was configured based on the principals described above. The machines used in these examples were the Roeders RXP500 DS model capable of 42,000 RPM and the Roeders RXD5 model capable of 50,000 RPM. The dental article milled in Example 24 was a central crown and included 9 machining steps. Example 25 was a molar crown and milling included 8 machining steps. The following Tables VIII and IX set forth the machining steps and their essential characteristics.

TABLE VIII

Example 24 Central Crown Program

| Machining Steps | Order of Execution | Feed Rate, F mm/min | Tool Diameter mm | Tool Diamond Grit microns | Depth of Cut microns | Feed per revolution, microns RXP500/RXD5 | |
|---|---|---|---|---|---|---|---|
| Drilling_inside_1_1.TAP | 1 (R) | 1500 | 1.3 | 126 | 50 | 36 | 30 |
| Milling_inside_2_1.TAP | 2 (R) | 2000 | 1.3 | 126 | 80 | 48 | 40 |
| Prep_rough1_inside_3_1.TAP | 3 (R) | 2000 | 1.3 | 126 | 100 | 48 | 40 |

TABLE VIII-continued

Example 24 Central Crown Program

| Machining Steps | Order of Execution | Feed Rate, F mm/min | Tool Diameter mm | Tool Diamond Grit microns | Depth of Cut microns | Feed per revolution, microns RXP500/ RXD5 | |
|---|---|---|---|---|---|---|---|
| Prep_rough1_outside_4_1.TAP | 4 (R) | 2000 | 1.3 | 126 | 100 | 48 | 40 |
| Drilling_outside_5_1.TAP | 5 (R) | 1500 | 1.3 | 126 | 70 | 36 | 30 |
| Prep_semi_6_1.TAP | 6 (I) | 1000 | 1.2 | 91 | 40 | 24 | 20 |
| Prep_fini_7_1.TAP | 7 (F) | 3000 | 0.5 | 91 | 22 | 71 | 60 |
| Milling_outside_8_1.TAP | 8 (I) | 1500 | 1.2 | 91 | 40 | 36 | 30 |
| Milling_outside_9_1.TAP | 9 (I) | 1500 | 1.2 | 91 | 65 | 36 | 30 |

R-rough machining,
I-intermediate machining,
F-fine machining

TABLE IX

Example 25 Molar Crown Program

| Machining Steps | Order of Execution | Feed Rate, F mm/min | Tool Diameter mm | Tool Diamond Grit microns | Depth of Cut microns | Feed per revolution, microns, RXP500/ RXD5 | |
|---|---|---|---|---|---|---|---|
| Drilling_inside_1_1.TAP | 1 (R) | 1500 | 1.3 | 126 | 50 | 36 | 30 |
| Milling_inside_2_1.TAP | 2 (R) | 2000 | 1.3 | 126 | 80 | 48 | 40 |
| Prep_rough1_inside_3_1.TAP | 3 (R) | 2000 | 1.3 | 126 | 100 | 48 | 40 |
| Prep_rough1_outside_4_1.TAP | 4 (R) | 2000 | 1.3 | 126 | 100 | 48 | 40 |
| Drilling_outside_5_1.TAP | 5 (R) | 1500 | 1.3 | 126 | 70 | 36 | 30 |
| Prep_semi_6_1.TAP | 6 (I) | 1000 | 1.2 | 91 | 40 | 24 | 20 |
| Prep_fini_7_1.TAP | 7 (F) | 3000 | 0.5 | 91 | 22 | 71 | 60 |
| Milling_outside_8_1.TAP | 8 (I) | 1500 | 1.2 | 91 | 70 | 36 | 30 |

R-rough machining,
I-intermediate machining,
F-fine machining

In the examples shown, the target accuracy of the margin at the preparation line was very high, within about 25 microns. Therefore, two machining steps, 6$^{th}$ and 7$^{th}$, were carried out internally to provide higher accuracy at the preparation line. The depth of cut (lateral lining) ranged from approximately 0.022 mm (22 microns) to approximately 0.10 mm (100 microns) for the two examples. To quantify accuracy, the milled parts were scanned with Renishaw Cyclon Scanner with an accuracy of 3 microns and the scan was compared with the corresponding CAD file in STL format using Geomagic® QUALIFY software. The accuracy (standard deviation) was measured to be 0.022 mm (22 microns).

Example 26

Example 26 illustrates the use of the "6-th axis" or loading robot attached to 5-axis CNC machine. A blank or block holder 22 is attached to a pallet having a transponder such as a radio-frequency identification (RFID) tag for providing information about the mill block, such as type of material, shade, strength, and other factors useful about the material. A sensor on the milling machine reads the RFID tag to determine the material on the pallet prior to the milling operation. A database linked to the milling machine associates a specific CAM file to the block of material and the machine mills the block in accordance with the CAM file. A pallet carrying a mill block is placed on a shelf of an automatic loading system from which it is automatically transferred to the housing of the CNC machine when the associated CAM file comes up for execution in the job queue. Such automated loading system can carry from hundred or less to few hundreds and even thousands units. This robotic feature is sometimes called "sixth axis".

When a new block is added to the holder and pallet, the information regarding the properties of the block of material may be input by an operator by the use of a barcode type scanner. The RFID tag is scanned and the control panel is programmed to erase the prior information associated with the previous block of material. The new material information is then entered into the control panel. A database stores the information about the block of material on the pallet. When a new case is ready to be milled, the CAM file associated with the block on the pallet is utilized to mill the block accordingly. Such automated loading/robotic system, available only for larger, industrial CNC machines noticeably shortens per unit fabrication time.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:
1. A block for machining a dental article comprising
   a ceramic block comprising a first pre-drilled hole on a first surface and second pre-drilled hole on a second surface, the second surface opposing the first surface;
   wherein the first and second pre-drilled holes provide space for insertion of a drill tool;
   wherein the first hole is deeper than the second hole;
   wherein the first hole allows the insertion of a drill into greater than half an entire depth of the block;
   wherein both first and second pre-drilled holes do not extend entirely through to the opposing surface.
2. A block for machining a dental article as claimed in claim 1 wherein the first hole provides access to an interior of the block for drilling the undersurface of a dental article.
3. A block for machining a dental article as claimed in claim 1 wherein the second hole provides access to an interior of the block for drilling the exterior surface of a dental article.

4. A block for machining a dental article as claimed in claim 3 wherein the exterior surface of a dental article comprises the occlusal area of a dental article.

5. A block for machining a dental article as claimed in claim 1 wherein the dental article comprises an inlay, an onlay, a bridge, an abutment, a facing, a veneer, a facet, a crown, a partial crown, a framework or a coping.

* * * * *